(12) United States Patent
Morishita et al.

(10) Patent No.: US 9,023,343 B2
(45) Date of Patent: May 5, 2015

(54) PHOSPHORYLATION-INHIBITING AGENT OR DEPHOSPHORYLATING AGENT FOR PTEN

(75) Inventors: Kazuhiro Morishita, Miyazaki (JP); Shingo Nakahata, Miyazaki (JP); Makoto Hamasaki, Miyazaki (JP)

(73) Assignee: Miyazaki Prefecture, Miyazaki (JP)

( * ) Notice: Subject to any disclaimer, the term of this patent is extended or adjusted under 35 U.S.C. 154(b) by 416 days.

(21) Appl. No.: 13/263,876

(22) PCT Filed: Mar. 26, 2010

(86) PCT No.: PCT/JP2010/055378
§ 371 (c)(1),
(2), (4) Date: Dec. 2, 2011

(87) PCT Pub. No.: WO2010/116899
PCT Pub. Date: Oct. 14, 2010

(65) Prior Publication Data
US 2012/0107299 A1 May 3, 2012

(30) Foreign Application Priority Data
Apr. 9, 2009 (JP) .................. 2009-095147

(51) Int. Cl.
A61K 38/46 (2006.01)
C12N 15/00 (2006.01)
G01N 33/53 (2006.01)
C12Q 1/48 (2006.01)
A61K 31/223 (2006.01)
A61K 31/7088 (2006.01)
C07K 16/40 (2006.01)
C07K 16/44 (2006.01)
C12N 9/12 (2006.01)
C12N 9/18 (2006.01)
A61K 48/00 (2006.01)

(52) U.S. Cl.
CPC .............. *C12Q 1/485* (2013.01); *A61K 31/223* (2013.01); *A61K 31/7088* (2013.01); *C07K 16/40* (2013.01); *C07K 16/44* (2013.01); *C07K 2317/34* (2013.01); *C12N 9/12* (2013.01); *C12N 9/18* (2013.01); *G01N 2500/00* (2013.01); *A61K 48/005* (2013.01)

(58) Field of Classification Search
CPC ........................ C07K 2317/34; A61K 48/005
See application file for complete search history.

(56) References Cited

U.S. PATENT DOCUMENTS

2007/0128194 A1  6/2007  Song et al.

FOREIGN PATENT DOCUMENTS

JP  2007-153864 A  6/2007

OTHER PUBLICATIONS

Ning et al, A novel leptin signalling pathway via PTEN inhibition in hypothalamic cell lines and pancreatic b-cells, The EMBO Journal (2006) 25, 2377-2387.*
Kim et al, NDRG2 expression decreases with tumor stages and regulates TCF/b-catenin signaling in human colon carcinoma, Carcinogenesis vol. 30 No. 4 pp. 598-605, 2009.*
Pise-Masison et al, Gene expression profiling of ATL patients: compilation of disease-related genes and evidence for TCF4 involvement in BIRC5 gene expression and cell viability, Blood, Apr. 23, 2009 vol. 113, No. 17, prepublished online Jan. 8, 2009.*
Hu et al, NDRG2 expression and mutation in human liver and pancreatic cancers, World J Gastroenterol 2004;10(23):3518-3521.*
Kim et al, NDRG2 suppresses cell proliferation through down-regulation of AP-1 activity in human colon carcinoma cells, Int. J. Cancer: 124, 7-15 (2009).*
Sakashita et al, Mutations of the p53 gene in adult T-cell leukemia, Blood, vol. 79, No. 2 [Jan. 15, 1992: pp. 477-480.*
Liu et al, Promoter methylation, mutation, and genomic deletion are involved in the decreased NDRG2 expression levels in several cancer cell lines, Biochem Biophys Res Commun, 358, 164-9.*
Lorentzen et al, Expression of NDRG2 is down-regulated in high-risk adenomas and colorectal carcinoma, BMC Cancer, 7, 192-9.*
Wang et al, NDRG2 is a new HIF-1 Target Gene Necessary for Hypoxia-Induced Apoptosis in A549 Cells, Cell Physiol Biochem, 21, 239-50.*
Steck, P., et al., Identification of a candidate tumour supressor gene, MMAC1, at chromosome 10q23.2 that is mutated in multiple advanced cancers, Nature Genetics, Apr. 15, 1997, pp. 356-362, vol. 15.
Li, J., et al., PTEN, a putative protein tyrosine phosphatase gene mutated in hum brain, breast, and prostate cancer, Science, Mar. 28, 1997, pp. 1943-1947, vol. 275.

(Continued)

*Primary Examiner* — Karlheinz R Skowronek
*Assistant Examiner* — Sergio Coffa
(74) *Attorney, Agent, or Firm* — Knobbe Martens Olson & Bear LLP

(57) ABSTRACT

Provided is a preventive, progression inhibitor or remedy for a disease one of the causes of which is the activation of the P13K/AKT signaling pathway or vice versa. A phosphorylation-inhibiting and/or dephosphorylating agent, which has an effect of inhibiting the phosphorylation at least at one of the phosphorylation sites of PTEN protein selected from the group consisting of T382, T383 and S380 and/or an effect of dephosphorylating the same, is prepared. Alternatively, a phosphorylation-inhibiting or dephosphorylating agent for PTEN is screened by a method comprising a step for confirming an ability of a test substance to inhibit the phosphorylation at least at one of the phosphorylation sites of PTEN protein selected from the group consisting of T382, T383 and S380 or a dephosphorylation ability thereof. Then, a substance having an effect opposite to the inhibition of PTEN phosphorylation or dephosphorylation thereof, e.g., an antibody against the phosphorylation-inhibiting or dephosphorylating agent for PTEN obtained above, is also obtained.

4 Claims, 19 Drawing Sheets

(56) References Cited

OTHER PUBLICATIONS

Li, D., et al, PTEN/MMAC1/TEP1 suppresses the tumorigenicity and induces G1 cell cycle arrest in human glioblastoma cells, Proc. Natl. Sci. USA, Dec. 1998, pp. 15406-15411, vol. 95.

Vivanco, I., The phosphatidylinositol 3-kinase-AKT pathway in human cancer, Nat. Rev. Cancer, Jul. 2002, pp. 489-501, vol. 2.

Keniry, M., et al, The role of PTEN signaling perturbations in cancer and in targeted therapy, Oncogene, 2008, pp. 5477-5485, vol. 27.

Leslie, N., et al, PTEN function: how normal cells control it and tumour cells lose it, Biochem. J., 2004, pp. 1-11, vol. 382.

Liu, N., et al, N-Myc downstream-regulated gene 2 is involved in p53-mediated apoptosis, Nucleic Acids Research, Aug. 9, 2008, pp. 5335-5349, vol. 36.

Park, Y., et al, SOCS1 induced by NDRG2 expression negatively regulates STAT3 activation in breast cancer cells, Biochemical and Biophysical Research Communications, Aug. 27, 2007, pp. 361-367, vol. 363.

Deng, Y., et al, N-Myc downstream-regulated gene 2, (NDRG2) inhibits glioblastoma cell proliferation, Int. J. Cancer, 2003, pp. 342-347, vol. 106.

Song, P, et al, Protein kinase Cs-dependent LKB1 serine 428 phosphorylation increases LKB1 nucleus export and apoptosis in endothelial cells, Journal of Biological Chemistry, May 2, 2008, pp. 12446-12455, vol. 283.

Odriozola, L, et al, Regulation of PTEN activity by its carboxyl-terminal autoinhibitory domain, The Journal of Biological Chemistry, Aug. 10, 2007, pp. 23306-23315, vol. 282.

Gajewski, J., et al, Expression, generation, and purification of unphosphorylated and phospho-Ser-380/THr-382/Thr-383 form of recombinant PTEM phosphatase., protein Expression and Purification, 2007, vol. 55, p. 334-342.

Yasunaga, J., and M. Matsuoka. "[HTLV-I and leukemogenesis]." *Uirusu* 56.2 (2006): 241-249.

\* cited by examiner (A)

(B)

(A)

(B)

(A)

|  | Number of specimens | Point mutation Presence | Absence |
|---|---|---|---|
| Specimens of leukemia cells from ATL patients | 34 | 0 | 34 |
| HTLV-1 infected cell lines, ATL-derived cell lines | 8 | 0 | 8 |
| T-ALL cell lines | 4 | 1 | 3 |
| Pancreatic cancer cells from patients | 10 | 0 | 10 |
| Solid cancer cell lines | 21 | 0 | 21 |

(B)

(A)

(B)

(A)

(B)

(B)

KK1

Su9T-01

(A)

(B)

(A)

(B)

PHOSPHORYLATION-INHIBITING AGENT OR DEPHOSPHORYLATING AGENT FOR PTEN

CROSS-REFERENCE TO RELATED APPLICATIONS

This application is the U.S. National Phase under 35. U.S.C. §371 of International Application PCT/JP2010/055378, filed Mar. 26, 2010, which claims priority to Japanese Patent Application No. 2009-095147, filed Apr. 9, 2009. The International Application was published under PCT Article 21(2) in a language other than English.

TECHNICAL FIELD

The present invention relates to a phosphorylation-inhibiting agent or dephosphorylating agent for PTEN. More particularly, the present invention relates to a phosphorylation-inhibiting or dephosphorylating agent for PTEN (Phosphatase and Tensin Homolog Deleted on Chromosome 10) to regulate the P13K/AKT signaling pathway, and also relates to a preventive or progression inhibitor for diseases associated with the P13K/AKT signaling pathway, comprising the same as an active ingredient.

BACKGROUND ART

PTEN gene is localized on chromosome 10q23.3 and identified as a tumor suppressor (non-patent documents 1 and 2). PTEN protein is widely expressed in the cells of the whole body and is known as an enzyme that catalyzes the dephosphorylation reaction of an inositol phospholipid, i.e., phosphatidylinositol 3,4,5-triphosphate (PIP3). PIP3 is synthesized in a cell by P13 kinase (P13K) and causes the activation of protein kinase B(PKB)/AKT. It is said that PTEN is responsible for this dephosphorylation reaction of PIP3 and has a function to convert PIP3 into phosphatidylinositol 4,5-bisphosphate (PIP2).

As mentioned above, PTEN negatively regulates the P13K/AKT signaling pathway (non-patent document 3). Conversely, when the activity of PTEN is inhibited, PIP3 accumulates in cells, thereby the P13K/AKT signaling pathway is activated. It is suggested that the constant activation of the P13K/AKT signaling pathway is involved in diabetes, autism, and some cancers (patent document 4). In addition, molecular modification of PTEN has been known to change its activity (non-patent documents 5 and 6). It is important to maintain the activity of PTEN for diagnosis and therapy of various diseases.

PRIOR ART DOCUMENTS

Non-Patent Documents

Non-patent document 1: Steck P A, Pershouse M A, Jasser S A, Yung W K, Lin H, Ligon A H, Langford L A, Baumgard M L, Hattier T, Davis T, Frye C, Hu R, Swedlund B, Teng D H and Tavtigian S V. (1997) "Identification of a candidate tumour suppressor gene, MMAC1, at chromosome 10q23.3 that is mutated in multiple advanced cancers." Nat. Genet. 15, 356-362.

Non-patent document 2: Li J, Yen C, Liaw D, Podsypanina K, Bose S, Wang S I, Puc J, Miliaresis C, Rodgers L, McCombie R, Bigner S H, Giovanella B C, Ittmann M, Tycko B, Hibshoosh H, Wigler M H, Parsons R. (1997) "PTEN, a putative protein tyrosine phosphatase gene mutated in human brain, breast, and prostate cancer." Science. 275, 1943-7.

Non-patent document 3: Li D M, Sun H. (1998) PTEN/MMAC1/TEP1 suppresses the tumorigenicity and induces G1 cell cycle arrest in human glioblastoma cells. Proc. Nat. Acad. Sci. 95: 15406-15411.

Non-patent document 4: Vivanco I, Sawyers C L. (2002) The phosphatidylinositol 3-Kinase AKT pathway in human cancer. Nat Rev Cancer. 2: 489-501. Review.

Non-patent document 5: Keniry M, Parsons R. (2008) The role of PTEN signaling perturbations in cancer and in targeted therapy. Oncogene 27: 5477-5485. Review.

Non-patent document 6: Leslie N R, Downes C P. (2004) PTEN function: how normal cells control it and tumour cells lose it. Biochem J. 2004; 382: 1-11. Review.

DISCLOSURE OF THE INVENTION

Problems to be Solved by the Invention

One of the objectives of the present invention is to provide a phosphorylation-inhibiting and/or dephosphorylating agent for PTEN, or to provide an action to phosphorylate PTEN.

A further objective of the present invention is to provide a preventive drug, progression inhibitor or therapeutic agent for various diseases the cause of which is the activation or inactivation in the P13K/AKT signaling pathway by phosphorylation of PTEN.

Means for Solving the Problems

Accordingly, as a result of intensive studies, the present inventors have demonstrated that phosphorylation inhibition and/or dephosphorylation is effective for the maintenance of a PTEN activity and have found that such a phosphorylation-inhibiting and/or dephosphorylating agent is effective for the suppression of the activation of the P13K/AKT signaling pathway associated with it, and further have succeeded in obtaining a substance having an effect opposite to the inhibition of the PTEN phosphorylation or dephosphorylation thereof. The present invention has been attained based on these findings.

The present invention relates to a phosphorylation-inhibiting and/or dephosphorylating agent, which has an effect of inhibiting the phosphorylation at least at one of the phosphorylation sites of PTEN protein selected from the group consisting of T382, T383 and S380 and/or has an effect of dephosphorylating the same.

The phosphorylation-inhibiting and/or dephosphorylating agent may be NDRG2 protein or a peptide fragment thereof.

The present invention also relates to a phosphorylation-inhibiting and/or dephosphorylating agent for PTEN comprising a polynucleotide encoding NDRG2 in the form which can be introduced into cells.

The present invention also relates to a preventive drug, progression inhibitor or therapeutic agent for a disease one of the causes of which is the activation of the P13K/AKT signaling pathway by the phosphorylation of PTEN, comprising as an active ingredient any one of the above phosphorylation-inhibiting and/or dephosphorylating agents.

The disease mentioned above may be one member selected from the group consisting of adult T cell leukemia (ATL), pancreatic cancer, autism, skin cancer, malignant lymphoma, prostate cancer, endometrial cancer, uterine cervix cancer, ovarian cancer, head and neck squamous cell cancer, esophagus cancer, bile duct cancer, prostate cancer, pheochromocytoma, penile cancer, osteosarcoma, and testicular cancer.

The present invention also relates to a screening method of a phosphorylation-inhibiting or dephosphorylating agent for PTEN, comprising the step of confirming an ability of a test substance to inhibit the phosphorylation at least at one of the phosphorylation sites of PTEN protein selected from the group consisting of T382, T383, and S380 or a dephosphorylation ability thereof.

The screening method may comprise the steps of:

contacting a test substance with PTEN protein wherein at least one of the phosphorylation sites of PTEN protein selected from the group consisting of T382, T383 and S380 is included, or with a peptide fragment thereof; and selecting the test substance by using an index such that at least one of the phosphorylation sites of PTEN protein selected from the group consisting of T382, T383 and S380 is dephosphorylated or inhibited for the phosphorylation.

The screening method may be used for screening a drug to prevent the activation of the P13K/AKT signaling pathway.

The present invention also relates to a phosphorylation-promoting agent for PTEN, comprising an antibody against NDRG2 protein or a peptide fragment thereof.

The present invention also relates to a therapeutic agent for a disease one of the causes of which is the inactivation of the P13K/AKT signaling pathway due to the dephosphorylation of PTEN, comprising the phosphorylation-promoting agent for PTEN.

The disease may be diabetes.

The present invention also relates to a method for inhibiting the phosphorylation at least at one of the phosphorylation sites of PTEN gene in HTLV1 or ATL cells, selected from the group consisting of T382, T383 and S380, and/or dephosphorylating the same, which method comprises the step of introducing a polynucleotide encoding NDRG2 into HTLV1 or ATL cells.

The present invention also relates to a method for inhibiting the phosphorylation at least at one of the phosphorylation sites of PTEN gene in KLM-1 or PK45-P cells, selected from the group consisting of T382, T383 and S380, and/or dephosphorylating the same, which method comprises the step of introducing a polynucleotide encoding NDRG2 into KLM-1 or PK45-P cells.

Effect of the Invention

According to the present invention, it is possible to inhibit the phosphorylation of PTEN or recover the phosphorylated PTEN to an activated state thus prevention of onset, progression inhibition, and therapeutic effects for various diseases, one of the causes of which is the activation of the P13K/AKT signaling pathway, can be expected. Alternatively, in the case of phosphorylation-promoting agents having an effect opposite to the above effect, prevention of onset, progression inhibition, and therapeutic effects for various diseases one of the causes of which is the inactivation of the P13K/AKT signaling pathway can be expected.

MODE FOR CARRYING OUT THE INVENTION

In the present invention, at first, a substance with an effect to inhibit PTEN from being phosphorylated and/or a substance with an effect to dephosphorylate the once phosphorylated PTEN is provided.

The "PTEN gene" as used herein is located on chromosome 10q23.3 in a living body, and is identified as a tumor suppressor. PTEN protein is referred to a protein encoded by this gene, and is known as an enzyme that catalyzes the dephosphorylation reaction of phosphatidylinositol 3,4,5-triphosphate (PIP3). In addition, in the present specification, unless otherwise specifically stated, simply "PTEN" refers to any of full-length proteins encoded by such PTEN genes and peptide fragments of PTEN proteins.

Figure 1:
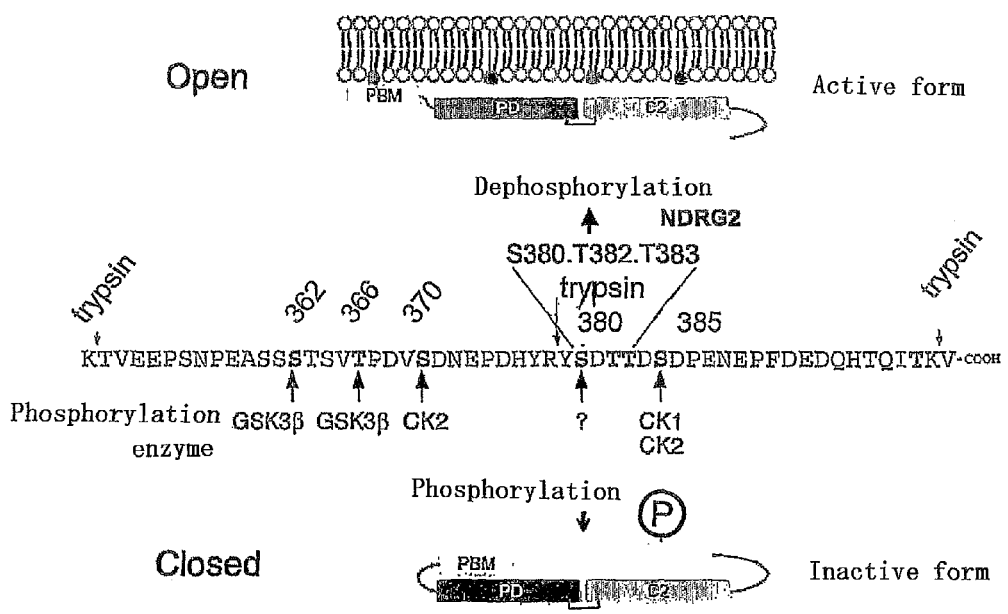
FIG. 1 shows phosphorylation-related sites of PTEN protein.

The "phosphorylation site of PTEN protein" is not particularly limited, but refers to at least the serine residue at position 380 (also referred to as S380 in the present specification), the threonine residue at position 382 (also referred to as T382 in the present specification), and the threonine residue at position 383 (also referred to as T383 in the present specification) among the amino acids constituting PTEN proteins in connection with the present invention. The expression of "PTEN is phosphorylated" or "PTEN protein is phosphorylated" means that one or two or more sites selected from the group consisting of these amino acid sites are phosphorylated. The term "dephosphorylation" refers to a state where one or two or all sites of the once phosphorylated sites of especially these residues are not phosphorylated (FIG. 1). Such a function can be examined by detecting the presence or absence of the dephosphorylation effect or the phosphorylation-inhibiting effect on phosphorylated PTEN proteins or peptide fragments of said proteins containing the phosphorylation site(s).

In the present invention, a desirable example of a substance having an effect to inhibit such PTEN from being phosphorylated and/or a substance having an effect to dephosphorylate the once phosphorylated PTEN includes, but not limited to, NDRG2, a gene encoding NDRG2, and a fragment thereof.

NDRG2 Gene

Figure 2:
FIG. 2 is a schematic view showing a domain structure of NDRG2.

Here, NDRG2 was discovered as a family of the NDRG1 gene the transcription of which is suppressed by the expression of N-myc. There are four kinds in this NDRG family, and the amino acid sequence homology between them is 57 to 65%. FIG. 2 shows the domain structure of the NDRG2 gene, and the structure has the common ndr region in the center and has a structure belonging to the superfamily of esterases and lipases. The common domain (ndr region)-like domain is the same α/β-hydrolase. The present inventors focused on the possibility of having its own phosphatase activity because NDRG2 possesses an esterase, α/β-hydrolase-like domain. The esterase and lipase contain bacterial lipase and choline esterase. These enzymes act on carboxyesters (EC:3.1.1.-). It is believed that three residues (three catalysts) are involved in the catalyst. That is, they are serine, a glutamic acid salt or an aspartic acid salt, and histidine. These catalyst residues may be involved in the nucleophilic effect on the carbonyl carbon atom of the ester bond. In contrast with other α/β-hydrolase fold family members, p-nitrobenzyl esterase and acetylchlorine esterase possess Glu instead of Asp at the active site of the carboxylic acid salt. The optimum hit score for this sequence is pfam03096.

NDRG2 Protein

The NDRG2 protein in the present invention may be any protein represented by the accession number, NP_057334.1, NP_963293.1, NP_963294.1, NP_963831.1, NP_963832.1, NP_963833.1, NP_963834.1, or NP_963835.1. In the present invention, the notation "NDRG2" includes a symbol representing a gene encoding NRDG2 or mRNA (GenBank registration number NM_016250.2, NM_201535.1, NM_201536.1, NM_201537.1, NM_201538.1, NM_201539.1, NM_201540.1, or NM_201541.1), and can be used interchangeably for the protein, gene and mRNA. Moreover, as a result of analysis of the base substitutions in the NDRG2 genome region by the present inventors, a mutation is observed in the exon 1, upstream, −89 base (C>T) in the two (MT2, ATL185 of 38 cases with ATL, and similarly in the base 147 (T>C) of the intron 4 in the two (SO4, ATL202) of 38 cases. Further, an amino acid substitution at position 26 (glutamine>glycine) in the exon 5, NDRG2 a-type, the base 77 (A>G) is found in the one (HUT102) of 38 cases. These genes, proteins, and other genes or proteins including mutations that can be found on bases or amino acids, and fragments thereof are also included in the definition of NDRG2 in the present invention.

Function of NRDG2

NDRG2 is expressed in various types of tissue cells, such as brain cells, muscle cells, and kidney cells (Hu, et al., Cell Tissue Res., 325: 67-76, 2006, Qu, et al., Mol. Cell. Biochem., 229: 35-44, 2002, etc.). As mentioned above, the NDRG2 genes are classified into four categories, and each has a high homology, but the expression is different from each other depending on the individual development and growth. It has been reported that NDRG2 is down-expressed in liver cancer, pancreatic cancer, meningioma, breast cancer cell lines, and lung cancer cell lines, and DNA methylation of the NDRG2 promoter region in liver cancer cell lines and meningioma has been proven (Xiao-Lan H, Xin-Ping L et al. NDRG2 expression and mutation in human liver and pancreatic Cancers. W J Gastroenterol 2004; 10 (23): 3518-3521; Eriks A L, Arie P et al. Integrative Genomic Analysis Identifies NDRG2 as a Candidate Tumor Suppressor Gene Frequently Inactivated in Clinically Aggressive Meningioma. Cancer Res 2005; 65: (16) 7121-7126)).

The substance having an effect to inhibit PTEN from being phosphorylated and/or the substance having an effect to dephosphorylate the once phosphorylated PTEN according to the present invention is effective as a preventive, progression inhibitor or therapeutic agent for a disease one of the causes of which is the activation of the P13K/AKT signaling pathway.

The disease one of the causes of which is the activation of the P13K/AKT signaling pathway includes, but not limited to, autism or cancer. Furthermore, the effectiveness of the PTEN phosphorylation inhibitor for the HTLV-1 infection and/or the ATL onset, the relationship of which was not clear heretofore, is confirmed by the present inventors, and such a disease is included within the scope of the present invention.

Autism is a condition characterized by qualitative disorder in interpersonal interaction, significant abnormality of communication or development disorder, remarkable confinement in the scope of activities and interests.

Cancer includes skin cancer, malignant lymphoma, prostate cancer, endometrial cancer, uterine cervix cancer, ovarian cancer, head and neck squamous cell cancer, esophagus cancer, bile duct cancer, prostate cancer, pheochromocytoma, penile cancer, osteosarcoma, and testicular cancer. Furthermore, cancer includes ATL.

Figure 3:
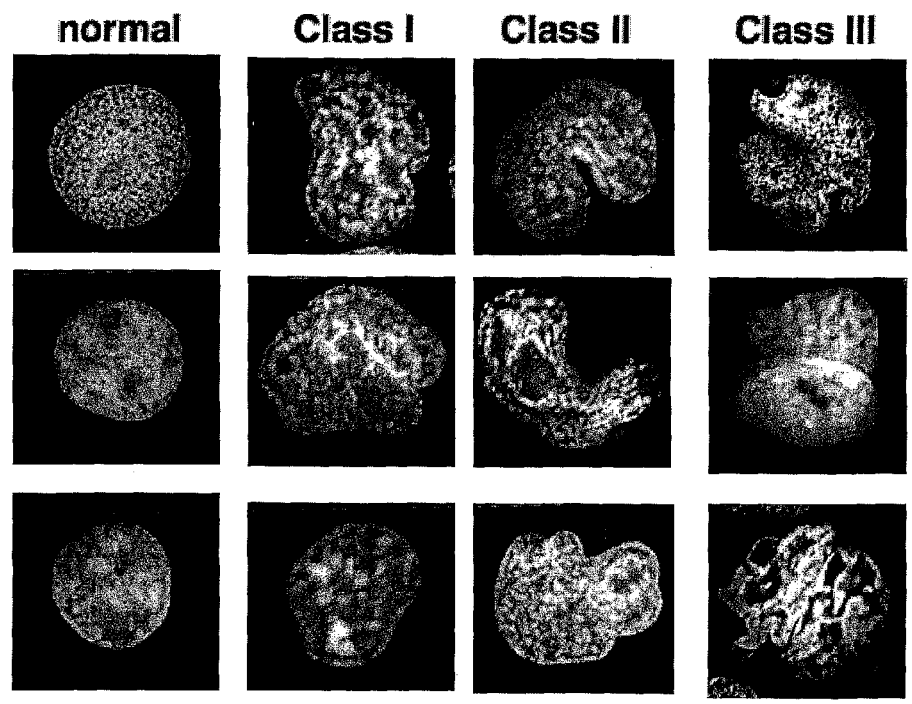
FIG. 3 is a photograph showing development of ATL and flower-like states of cells.

ATL (Adult T cell leukemia) refers to a viral leukemia caused by the infection of T cells with human T cell leukemia virus (HTLV-1), and it is the disease occurred due to the tumorigenesis of HTLV-1 infected T cells. The ATL has characteristic clinical findings, such that ATL has the peak of the onset from 50 years old to 60 years old generation; it progresses from a sub-acute state to a chronic state, develops rapidly to the end, and its prognosis is poor; the origin of the tumor cells is a T-cell, and a leukemia cell (flower like cell) having a notch or a segmented nucleus appears in the peripheral blood to accompany highly frequently with lymphadenopathy, hepatomegaly, and splenomegaly; and a skin lesion is frequently associated with ATL. The appearance of flower like state of the cell nuclei associated with the development of ATL is shown in FIG. 3.

Here, HTLV-1 is transferred to the nucleus of human T cells as the host with human retroviruses, to generate cDNA from RNA by reverse transcription, and cDNA is integrated into the host genome DNA.

The present invention also relates to a phosphorylating agent of PTEN, and such an agent is effective as a preventive, progression inhibitor or therapeutic agent for a disease one of the causes of which is the inactivation of the P13K/AKT signaling pathway.

Such diseases include diabetes. Diabetes is caused by abnormalities in glucose metabolism, manifesting a symptom such as a pathological rise of blood sugar level. In addition, the rise of blood sugar level can cause various complications. Genetic polymorphisms of PTEN are observed in many Japanese patients with type 2 diabetes, and insulin signaling is reduced by increased expression of PTEN, thereby to induce an insulin resistance, suggesting the possibility involved in the onset of type 2 diabetes.

Scope of NDRG2 Phosphorylation-Inhibiting and/or Dephosphorylating Agents, and Remedies The phosphorylation-inhibiting and/or dephosphorylating agents for PTEN, and the therapeutic agent comprising the same as an active ingredient for a disease one of the causes of which is the activation of the P13K/AKT signaling pathway, provided by the present invention, include a gene therapy agent comprising a polynucleotide encoding NDRG2 in the form introducible into a cell, NDRG2 protein, and a peptide fragment of the NDRG2 protein. As the NDRG2 gene, for example, NDRG2 derived from dendritic cells differentiated from a human T-ALL-derived cell line (MOLT4), a human peripheral blood monocyte, or a cord blood stem cell (PCT/KR2004/000634) can be used. The NDRG2 protein and antibodies against the NDRG2 protein and peptide fragments thereof may be synthesized by the chemical or genetic engineering method according to the common method.

In the present invention, the "therapy" includes an amelioration of symptoms in addition to a complete cure.

Preparation Method of Gene Drug

As a substance capable of controlling the activity of PTEN, the phosphorylation-inhibiting and/or dephosphorylating agents for PTEN, comprising as an active ingredient NDRG2 gene, and the therapeutic agent (hereinafter referred to as a gene drug) for a disease comprising the same as an active ingredient can be prepared, for example, by the following method. The gene drug as used herein is included preferably in a form enabling a polynucleotide encoding NDRG2 to be introduced into cells, provided that it can forcibly express mRNA and protein. A conventional method can be employed for enabling a polynucleotide encoding NDRG2 to take a form that can be introduced into cells. For example, a polynucleotide is directly introduced (see U.S. Pat. No. 5,580,859), or a formulation in the form of a recombinant virus vector is introduced. Moreover, non-viral introduction methods are also known, and these methods can be appropriately selected and used in the present invention.

Preparation Method of NDRG2 Gene Drug

As a virus vector suitable for cell introduction, vectors derived from the genomes of viruses selected from Baculoviridae, Parvoviridae, Picornoviridiae, Herpesveridiae, Poxyiridae, Adenoviridiae, Paramyxoviridiae, or Picornnaviridiae are used. Chimeric vectors may also be employed which exploit advantageous merits of each of the parent vector properties. Such viral genomes can be modified to be replication deficient, conditionally replicating or replication competent. More specifically, in the case where the vector is derived from an adenovirus, for example, a replication incompetent vector derived from human adenovirus genome (see U.S. Pat. Nos. 6,096,718; 6,110,458; 6,113,913; and 5,631,236), and an adeno-associated virus can be used. In the case of retroviral genome-derived vectors, they includes vectors based upon murine leukemia virus (MuLV), gibbon ape leukemia virus (GaLV), simian immuno deficiency virus (SIV), human immuno deficiency virus (HIV), and combinations thereof (see, e.g., U.S. Pat. Nos. 6,117,681; 6,107,478; 5,658,775; and 5,449,614; and Buchscher (1992), J. Virol. 66: 2731-2739; Johann (1992), J. Virol. 66: 1635-1640). In addition, a Sendai virus belonging to Paramyxoviridae (HVJ) also can be preferably used. In this case, after introducing a polynucleotide expression vector into tissues or cells extracted from a living body, such tissues or cells may be returned to the living body (ex vivo method). For example, an expression vector into which a polynucleotide is incorporated is introduced into cells by the conventional transfection method such as microinjection method and electroporation method.

Use Method of NDRG2 Gene Drug

In the virus vector or expression vector, the polynucleotide can be applied in a connected form under the control of an arbitrary promoter so that it is expressed systemically or specifically to the blood cell. Additionally, it is possible to deliver the NDRG2 gene to desired cells and efficiently express NDRG2 by making free use of the known drug delivery method such as an emulsion DDS method and a liposome method.

Preparation Method of NDRG2 Protein Drug

In the preparation of the dephosphorylating agent for PTEN comprising NDRG2 protein as an active ingredient, and the cancer therapeutic agent comprising this dephosphorylating agent as an active ingredient (hereinafter referred to as a "protein drug"), it is necessary to extract the NDRG2 protein (polypeptide) or produce it. Genetic engineering methods using a polynucleotide encoding NDRG2 are suitable for the production of the NDRG2 at low cost in large quantities. In addition, NDRG2 polypeptide can be obtained as an expression product in prokaryotic cells (e.g., *E. coli* and

*Bacillus subtilis*) or eukaryotic cells (e.g., yeast, insect cells, and mammal cells) if integrating this polynucleotide into a suitable expression vector by the known method. The NDRG2 polypeptide also can be synthesized according to the well-known chemical synthesis methods (for example, Merrifield, R. B. J. Solid phase peptide synthesis I. The synthesis of tetrapeptide. J. Amer. Chem. Soc. 85, 2149-2154, 1963; Fmoc Solid Phase Peptide Synthesis. A Practical Approach. Chan, W. C. and White, P. D., Oxford University Press, 2000).

Preparation Method of NDRG2 Protein Drug

The present protein drug also includes a "peptide derivative". The peptide derivative may contain a modification for promoting physical/chemical stabilization when introduced into the body, an activation modification such as in vivo metabolic stability and instability and an activation modification such as in vivo metabolic conditioning. The modifications for producing the peptide derivatives include acetylation, acylation, ADP-ribosylation, amidation, covalent bonding of flavine, covalent bonding of a heme moiety, covalent bonding of a nucleotide or nucleotide derivative, covalent bonding of a lipid or lipid derivative, covalent bonding of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, lipid attachment, sulfation, and selenoylation. It is possible to prepare a functional group occurring as the side chain of the amino acid residues, or as the N-terminal, or as the C-terminal, so long as any toxicities are not given to the composition containing the NDRG2 polypeptide while retaining its activity. For example, in order to extend the remaining of the parent polypeptide in blood or cells, the peptide derivative includes a derivative containing polyethylene glycol side chain, or an aliphatic carboxylic ester, a carboxylic amide formed by the reaction between the carboxyl group and ammonia or primary or secondary amine, an N-acyl derivative formed by the reaction between an acyl moiety (e.g., alkanoyl group or carbocyclic aroyl group) and a free amino group of an amino acid residue, and an O-acyl derivative formed by the reaction between an acyl moiety and a free hydroxyl group (e.g., the hydroxyl group of serine or threonine residue).

Preparation Method of NDRG2 Protein Drug

The NDRG2-containing drug may also include a pharmacologically acceptable "salt". This salt means both of a salt of the carboxyl group of the polypeptide and an acid addition salt of the amino group thereof. The salt of the carboxyl group may be formed by a well-known method. For example, the salt includes an inorganic salt formed by using sodium, calcium, ammonium, iron or zinc, and a salt with an organic base formed by using an amine such as triethanolamine, arginine or lysine, piperidine, and procaine. The acid addition salt includes, for example, a salt with a mineral acid (e.g., hydrochloric acid or sulfuric acid) and a salt with an organic acid (e.g., acetic acid or oxalic acid). All such salts may be provided in the form of retaining the activity of NDRG2.

Use Method of NDRG2 Protein Drug

In order to formulate the NDRG2 polypeptide into a form introducible into cells, the well-known means can be employed. For example, such means is the use of a fusion polypeptide wherein a cell membrane-permeable peptide is connected to the N-terminal of the polypeptide. The fusion polypeptide can be produced by the genetic engineering with use of a fusion polynucleotide. In the case of intracellular introduction of the NDRG2 polypeptide by the ex vivo method, such introduction is also possible with a lipid (BioPORTER: Gene Therapy Systems, USA, Chariot: Inc. Active Motif, USA).

NDRG2 Antibody Drug

In the present invention, a therapeutic agent comprising as an active ingredient a phosphorylating agent for PTEN comprising as an active ingredient an antibody against NDRG2 protein or a peptide fragment thereof (hereinafter referred to as an "antibody drug") also can be prepared. A well-known method can be used for such a preparation. Here, the antibody against NDRG2 protein or a peptide thereof refers to protein or a variant thereof that is produced in the living body by the stimulation of an antigen of NDRG2 in the immune reaction and specifically binds to the NDRG2 protein. The monoclonal antibody is especially suitable though it is possible to use the polyclonal antibody as well as the monoclonal antibody. Further, the antibody includes human antibodies, humanized antibodies, polyfunctional antibodies, chimeric antibodies, and anti-idiotype antibodies, and fragments thereof (e.g., F(ab')2 and Fab fragments), and other recombinant conjugates. These antibodies may be fused with an enzyme (e.g., alkaline phosphatase, horseradish peroxidase, and α-galactosidase) via a covalent bond or by recombination.

The antibody is usually produced by administering NDRG2 protein or its peptide fragment containing an antigen to an appropriate animal, and immunizing it. The monoclonal antibodies include all immunoglobulin molecules and Fab molecules, F(ab')2 fragments, Fv fragments, and other molecules exhibiting the immunological binding property of the original monoclonal and antibody molecules. Methods for producing polyclonal antibodies and monoclonal antibodies are well known in the art.

For example, the polyclonal antibodies are prepared by administering a purified specimen of the whole or a partial fragment of a polypeptide constituting the NDRG2 protein, or a peptide having a portion of the amino acid sequence of the protein, as an antigen, to an animal. In the production of antibodies, a rabbit, a goat, a rat, a mouse, a hamster, or the like can be used as an animal to which an antigen is administered. When a peptide that is a fragment of NDRG2 protein is used as an antigen, the peptide may be bonded via a covalent bond to a carrier protein, such as keyhole limpet haemocyanin, bovine thyroglobulin, or the like, and used as an antigen. The antigen is administered every 1 to 2 weeks after a first administration a total 2 to 10 times. Blood is collected 3 to 7 days after each administration, and the reactivity of the serum with the antigen used in the immunization is confirmed by an enzyme immunoassay. The serum is obtained from a non-human mammal whose serum exhibits a sufficient antibody titer to an antigen, and polyclonal antibodies can be isolated from the serum and purified using the well-known techniques.

On the other hand, in order to prepare monoclonal antibodies, for example, at first a rat whose serum exhibits a sufficient antibody titer to the NDRG2 protein or fragments thereof is used as a source for antibody-producing cells, which are fused with myeloma cells to prepare hybridomas. Thereafter, a hybridoma that specifically reacts with the NDRG2 protein or its polypeptide fragment is selected using an enzyme immunoassay or other methods. A monoclonal antibody with desired properties is produced from the thus obtained hybridoma and can be used as an antibody drug.

The present invention also provides a screening method of a phosphorylation-inhibiting or dephosphorylating agent for PTEN, comprising the step of confirming an ability of a test substance to inhibit the phosphorylation at least at one of the phosphorylation sites of PTEN protein selected from the group consisting of T382, T383 and S380 or a dephosphorylation ability thereof. Here, the test substance may be any of synthetic or naturally occurring low molecular weight compounds, genes, proteins, antibodies, and the like derived from biological substances.

The PTEN used in the screening method of the present invention is not particularly limited, but it is possible to use any of short synthetic peptide fragments containing the phosphorylation sites of T382, T383, and S380, or PTEN protein itself. Among these, the relatively short synthetic peptides are preferable because of their easy handling. In addition, when the PTEN protein itself is used, it is also possible to purify the PTEN protein expressed in, for example, ATL cell lines by an immunoprecipitation method and use it. Alternatively, it is also possible to contact a PTEN expression cell in a state to be phosphorylated, with a test substance, or further possible to contact DNA corresponding to the functional sites of PTEN with DNA corresponding to the test substance in the same cell by forced co-expression. Such contact can be performed using any known means, such as mixing in the same reaction solution, charging in the culture solution, and maintaining in the same cell. The reaction conditions are not particularly limited, but the reaction may be carried out at about room temperature (20° C. to 40° C.) or at a temperature suitable for culture for several minutes to several hours. After the reaction, it is possible to confirm the effect of dephosphorylation in a test substance or the effect of inhibiting the phosphorylation in a test substance by measuring the phosphorylation state of PTEN. Such measurement is not particularly limited, but it may be performed by examining the state of the reaction with the antibody using, for example, various PTEN phosphorylation antibodies corresponding to the site to be measured.

In the present invention, the effect of a test substance on phosphorylation inhibition and/or dephosphorylation for PTEN can be examined by confirming an ability to inhibit the phosphorylation at least at one of the phosphorylation sites of PTEN protein selected from the group consisting of T382, T383 and S380 or a dephosphorylation ability thereof. If the test substance has an ability to dephosphorylate at least one of the phosphorylation sites mentioned above, said test substance makes it possible to recover the activity of PTEN and regulate the P13K/AKT signaling pathway to an inert state. This, in turn, indicates that such a compound is effective for the prevention, development, or therapy of diseases induced by the activation of the P13K/AKT signaling pathway.

Figure 4:
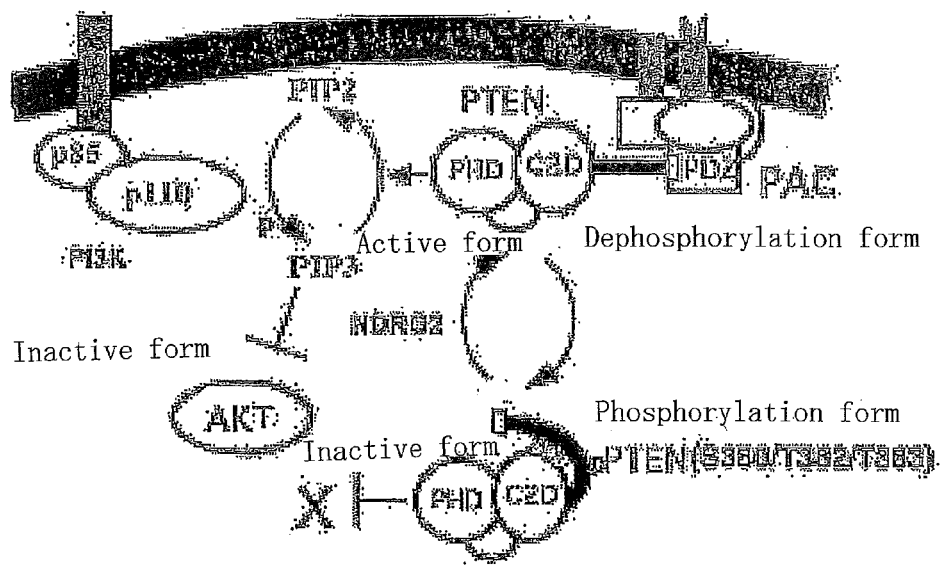
FIG. 4 shows an involvement chart including PTEN and also NDRG2 in the P13K/AKT signaling pathway, wherein (A) is a normal state of the P13K/AKT signaling pathway and (B) is a cancerous state thereof.
Figure 4:
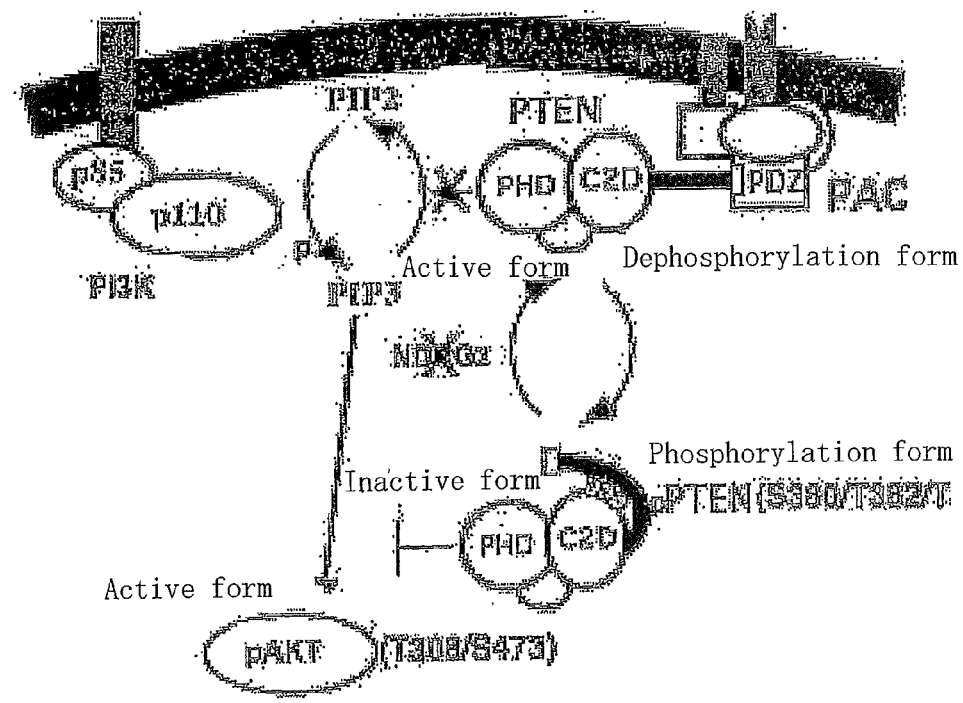

The present inventors have found the role of the P13K/AKT signaling pathway of NDRG2, and thus have developed such a screening method. In other words, new findings related to the P13K/AKT signaling pathway have been obtained by the present invention. FIG. 4 shows the P13K/AKT signaling pathway. In FIG. 4(A), a sufficient amount of NDRG2 is present in many cells in the normal state, wherein the dephosphorylation state is maintained at serine residue 380, threonine residue 382, and threonine residue 383 (S380/T382/T383) of PTEN, and the PIP3 phosphatase activity that PTEN itself possesses is in an active form. As for the signaling understream of the P13K signaling, in this state, PIP3 which is a substrate is dephosphorylated to PIP2 by the action of PTEN, and thus the level of PIP3 is decreased, resulting in the inhibition of the signaling that leads to AKT. However, as shown in FIG. 4(B), in several cancers including ATL, a decreased expression of NDRG2 due to genomic abnormalities makes it impossible to maintain the PTEN protein as the dephosphorylated form so that PTEN (S380/T382/T383) is phosphorylated with a certain PTEN phosphorylation enzyme, the structure of the PTEN protein is changed, and PTEN becomes an inactivated type protein of which enzymatic activity as the PIP3 phosphatase is inactivated. Then, when P13K is activated by the information from the receptor, production of PIP3 is increased to promote AKT phosphorylation, thereby to enhance the cell proliferation ability and the apoptosis-inhibiting ability in the downstream, leading to the immortalization of cells. In general, when P13K is activated by insulin or a proliferation factor, PIP2 which is a phospholipid is phosphorylated to PIP3, and then PIP3 activates PDK1 by phosphorylation. The activated PDK1 activates AKT by phosphorylation. The activated AKT promotes the differentiation and proliferation of cells. PTEN, as described above, is a phosphatase that returns this PIP3 to PIP2 by dephosphorylation, and negatively regulates the P13K/AKT signaling pathway.

In the present invention, it is possible to screen substances to correct the disorder of the negative control in the P13K/AKT signaling pathway. Therefore, the screening method of the present invention is involved in the P13K/AKT signaling pathways, and it is also a screening method for drugs which can be used for prevention, therapy, and progression inhibition for diseases. Such diseases include, but not limited to, autism, skin cancer, malignant lymphoma, prostate cancer, endometrial cancer, uterine cervix cancer, ovarian cancer, head and neck squamous cell cancer, esophagus cancer, bile duct cancer, prostate cancer, pheochromocytoma, penile cancer, osteosarcoma, and testicular cancer.

The phosphorylation-inhibiting and/or dephosphorylating agent for PTEN, or the phosphorylating agent for PTEN according to the present invention is provided as a parenteral or oral formulation. In the case of parenteral use, the gene introduction method can be effectively used, but not limited to it.

In the case of parenteral use, the agent may be mixed with suitable excipients, adjuvants, and/or pharmaceutically acceptable carriers and administered to a patient alone or in combination with other agents. Examples of the carrier that is especially preferably used include, but not limited to, saline, buffered saline, dextrose, and water. In one embodiment of the present invention, the pharmaceutically acceptable carrier is pharmaceutically inert.

For parenteral administration, intra-arterial (e.g., through the carotid artery), intramuscular, subcutaneous, intramedullary, intrathecal, intracerebroventricular, intravenous, intraperitoneal, or intranasal administration may be performed.

Oral formulations may take any form, such as powders, granules, finely divided powders, dry syrups, tablets, capsules, injections, and solutions. In addition, depending on the dosage form, the oral formulations can be prepared by appropriately mixing or diluting/dissolving with drug additives, such as suitable excipients; disintegrating agents; binders; lubricants; diluents; buffers (e.g., phosphoric acid, citric acid, succinic acid, acetic acid, and other organic acids or salts thereof); isotonic agents; preservatives; wetting agents; emulsifiers; dispersants; stabilizers; solubilizers; antioxidants such as ascorbic acid; low molecular weight (less than about 10 residues) polypeptides (e.g., polyarginine or tripeptide); proteins (e.g., serum albumin, gelatin, or immunoglobulins); hydrophilic polymers (e.g., polyvinylpyrrolidone); amino acids (e.g., glycine, glutamic acid, aspartic acid, or arginine); monosaccharides, disaccharides and other carbohydrates (including cellulose or its derivatives, glucose, mannose, or dextrin); chelating agents (e.g., EDTA); sugar alcohols (e.g., mannitol or sorbitol); counterions (e.g., sodium); and/or nonionic surfactants (e.g., polysorbates and poloxamers), according to the pharmaceutically known techniques. Such substances that enhance isotonicity and chemical stability are non-toxic to recipients at the dosages and concentrations used.

Techniques for formulation and administration are described, for example, in the latest edition of the Japanese Pharmacopoeia and its latest supplement, and in the final version of "REMINGTON'S PHARMACEUTICAL SCIENCES" (Maack Publishing Co., Easton, Pa.).

The phosphorylation-inhibiting and/or dephosphorylating agent of the present invention is a drug contained in an amount effective to achieve the intended purpose of the desired drug, and the "therapeutically effective amount" or "pharmacologically effective amount" is well recognized by a person ordinarily skilled in the art, and refers to an amount of a drug effective to produce a pharmacological result. Determination of the therapeutically effective amount is well known to a person ordinarily skilled in the art.

The therapeutically effective amount refers to an amount of the drug to alleviate the disease state by the administration. The therapeutic effect and toxicity of such compounds may be determined by standard pharmaceutical procedures in cell cultures or experimental animals. The dose is preferably in the range of circulating concentrations that include the ED50 with no or little toxicity. This dose varies within this range depending on the dosage form used, sensitivity of patients, and administration route. As an example, the dose of a composite is appropriately chosen depending on the age or other conditions of patients, the kind of the disease, and the kind of the composite to be used.

Hereinafter, the present invention will be described more specifically based on Examples. However, these Examples show only embodiments of the present invention, and the present invention is not construed as being limited by the following Examples.

Example 1

Identification of Phosphorylation Abnormalities in PTEN Protein in Various Cancer Cells Including ATL 1. Quantitative Real Time RT-PCR PTEN specific primers (Forward 5'-CAGCCATCAT-CAAAGAGATCG-3' (SEQ ID NO: 1 in the Sequence Listing), Reverse 5'-AAAAGGATATTGTGCAACTCTGC-3' (SEQ ID NO: 2 in the Sequence Listing)), β-actin specific primers (Forward 5'-GACAGGATGCAGAAGGAGAT-TACT-3' (SEQ ID NO: 3 in the Sequence Listing), Reverse 5'-TGATCCACATCTGCTGGAAGGT-3' (SEQ ID NO: 4 in the Sequence Listing)), SYBR GREEN® PCR Master Mix (Applied Biosystems), and cDNA as a template were mixed, and 40 cycles (one cycle: 95° C., 10 seconds; 60° C., 60 seconds) of PCR reaction were performed using an ABI PRISM® 7000 Sequence Detection System. The data were analyzed using the Crossing Point Method to determine the Ct (Threshold Cycle) value from the intersection point of the amplification curve and the threshold value. The expression levels of PTEN mRNA and β-actin mRNA were calculated based on the calibration curve prepared using the obtained Ct values and serial dilutions of a standard sample (cDNA derived from MOLT4 cells), and the expression level of PTEN gene/expression level of β-actin gene in each specimen was calculated. The obtained value was corrected by dividing it by a value of the standard specimen.

2. Analysis of PTEN Gene Expression

The expression level of PTEN mRNA was quantified by the quantitative real time RT-PCR method using four T-ALL cell lines (Jurkat, MOLT4, MKB-1, KAWAI), two HTLV-1 infected cell lines (HUT102, MT2) and six ATL cell lines (ED-40515 (-), Su9T-01, SiT, KOB, KK1, SO4). As a result, eight cell lines of the HTLV-1 infected cell lines and the ATL cell lines tended to show a small increase in the expression level compared to the four T-ALL cell lines [FIG. 5(A)]. Further, analysis of PTEN gene expression was carried out by the quantitative real time RT-PCR method using 5 cases of CD4+ T cells derived from healthy subjects and 7 cases of acute ATL cells derived from patients, revealing that there was no significant difference in the expression level among them [FIG. 5(B)].

3. Analysis of Point Mutation

The primers (see Table 1: SEQ ID NOs 5 to 26 in the Sequence Listing) for each exon of PTEN gene was prepared and amplified by 40 cycles of PCR reaction (98° C. for 10 seconds, specific annealing temperature for each exon for 30 seconds, 72° C. for 45 seconds) using 200 ng of genomic DNA as a template. The PCR products were treated with phenol-chloroform, purified by ethanol precipitation, and sequence PCR reactions were performed with primers specific for each exon, followed by determination of the base sequence with Applied Biosystem 3130 Genetic Analyzer. The analysis was performed in comparison with the registered nucleotide sequences by Clustal X (http://www-igb-mc.u-strasbg.fr/BioInfo/).

TABLE 1

|  | Forward | Reverse | AT* |
|---|---|---|---|
| exon1 | GGCATCAGCTACCGCCAAGT (5) | CCAAACTACGGACATTTTCG (6) | 50 |
| exon2 | TGAAGACCATAACCCACCAC (7) | CCTTGTCATTATCTGCACGC (8) | 50 |
| exon3 | TAATTTCAAATGTTAGCTCAT (9) | AAGATATTTGCAAGCATACAA (10) | 50 |
| exon4 | GTTTGTTAGTATTAGTACTTT (11) | ACAACATAGTACAGTACATTC (12) | 50 |
| exon5a | TATTCTGAGGTTATCTTTTA (13) | CTTTCCAGCTTTACAGTGAA (14) | 50 |
| exon5b | GCTAAGTGAAGATGACAATCA (15) | AGGAAAAACATCAAAAAATAA (16) | 50 |
| exon6 | TTGGCTTCTCTTTTTTTTCTG (17) | ACATGGAAGGATGAGAATTTC (18) | 50 |
| exon7 | CCTGTGAAATAATACTGGTATG (19) | CTCCCAATGAAGTAAAGTACA (20) | 50 |
| exon8a | TTAAATATGTCATTTCATTTCTTTTTC (21) | CTTTGTCTTTATTTGCTTTGT (22) | 50 |

TABLE 1-continued

| Forward | Reverse | AT* |
|---|---|---|
| exon8b GTGCAGATAATGACAAGGAATA(23) | ACACATCACATACATACAAGTC(24) | 55 |
| exon9 TTCATTTTAAATTTTCTTTCT(25) | TGGTGTTTTATCCCTCTTGAT(26) | 50 |

AT indicates an annealing temperature (° C.).
In parentheses, SEQ ID NOs of the Sequence Listings are shown.

Figure 6:
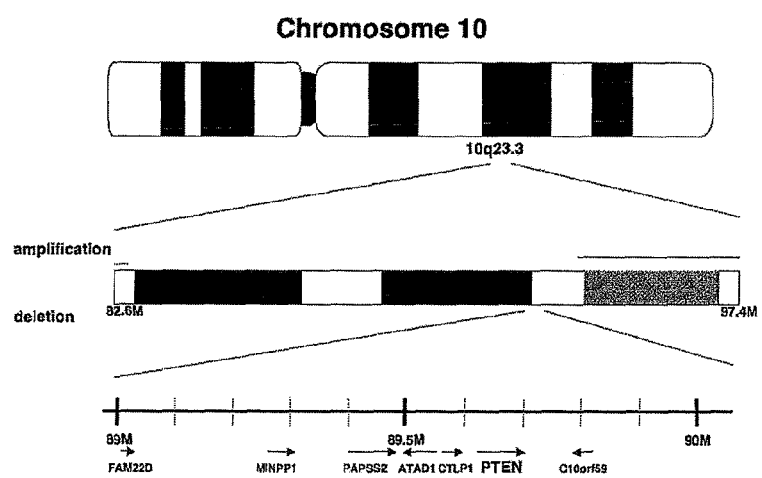
FIG. 6(A) is a table showing the search result of a point mutation of PTEN gene in leukemia cell lines or patient-derived cells.
FIG. 6(B) is a schematic view showing the result of genome analysis of the region where PTEN is present.

As a result, the base sequence for each exon was determined using the cell lines used in the study as well as genomic DNA from patient samples, and a search for point mutation in the sequence was performed, resulting in that a 9-base insertion including a 2-base deletion (234 amino acid residues) and a 39-base insertion including the stop codon (246 amino acid residues) were recognized in the T-ALL cell line Jurkat, but genomic abnormalities were not observed at all in other cell lines [FIG. 6(A)].

4. Multi-fluorescent Chromosome Analysis (Spectral Karyotyping SKY) and DAPI Banding Analysis Analysis of chromosome abnormalities was performed by combining multi-fluorescent chromosome analysis (spectral karyotyping SKY) with DAPI (4,6-diaminido-2-phenylindole dihydrochloride) staining based on the publication of Kakazu et al. (Kakazu N, TaniwakiM, Horiike S, et al. Combined spectral karyotyping and DAPI banding analysis of chromosome abnormalities in myelodysplastic syndrome. Gene Chromosome Cancer. 1999; 26: 336-345.). After denaturation of the chromosomes from the cells immobilized on a slide glass, they were hybridized with a probe for SKY (Applied Spectral Imaging Inc.) at 37° C. for 2 days. Detection of SKY signals was performed according to the protocol of Applied Spectral Imaging Inc. The chromosomes were counterstained by a combination of DAPI with an antifading solution (Vectaschield; Vector Laboratories). Images were acquired by an SD200 Spectracube (Applied Spectral Imaging) mounted on an Olympus BX50-RF (Olympus) with a SKY-1 optical filter (Chroma Technology). Ten to twenty metaphase chromosomal images were respectively analyzed and karyotypes were described according to the ISCN1995.

5. High-Density SNP Array Comparative Genomic Hybridization (Array CGH) Analysis Complete genomic DNA was cleaved by a restriction enzyme XbaI, and a single-primer PCR amplification was performed after adapter ligation. After treatment with DNase I, 40 μg of PCR products were labeled with biotin, and hybridized to the array. Each SNP was scored using GTYPE 4.1 software (Affymertix). Chromosome copy numbers and LOH (Loss of heterozygosity) were detected by ACUE 2.1 (Mitsui Knowledge Industry, Tokyo, http://bio.mki.co.jp/en/product/acue2/index.html) and CNAG 2.0 (Nannya Y, Sanada M, Nakazaki K, et al. A Robust Algorithm for Copy Number Detection Using High-Density Oligonucleotide Single Nucleotide Polymorphism Genotyping Arrays. Cancer Res. 2005; 65: 6071-6079.). Data standardization was performed on the basis of six normal specimens. Genomic location of probes on the array is according to NCBI genome map build 35.1.

6. Analysis of Genomic Abnormalities in the 10q23 Region

For ATL leukemia cells, genome analysis by the SNP array CGH method and the SKY/FISH method was performed for 61 cases in the 10q23 region where PTEN was present. Accumulation of the genomic abnormalities such as genomic deletion was not recognized in this region (FIG. 6(B)).

7. Identification of Abnormalities in PTEN Phosphorylation in ATL, and Decreased Expression of NDRG2 Protein (1) Test Antibodies Rabbit anti-human NDRG2 antibody was produced by synthesizing an NDRG2 peptide (NDRG2 type B (NP_057334), 17-31 amino acid residues, PGQTPEAAKTHS-VET), immunizing rabbits with the synthetic peptide, purifying IgG fractions from the serum after immunization, and performing purification with a peptide-immobilized column. Other antibodies, such as mouse anti-β-actin (AC-15) monoclonal antibody (A5441), mouse anti-α-tubulin (DM1A) monoclonal antibody (T9026), rabbit anti-FLAG polyclonal antibody (F7425), mouse anti-FLAG (M2) monoclonal antibody (F1804) (SIGMA ALDRICH), mouse anti-PTEN (26H9) monoclonal antibody (#9556), rabbit anti-Phospho-PTEN (Ser380/Thr382/383) polyclonal antibody (#9554), rabbit anti-phospho-AKT (Ser473) polyclonal antibody (#9271), rabbit anti-phospho-AKT (Thr308) polyclonal antibody (#9275), rabbit anti-AKT polyclonal antibody (#9272), rabbit anti-phospho-PTEN (Ser380) polyclonal antibody (#9551), rabbit anti-Fox01 polyclonal antibody (#9462) (Cell Signaling TECHNOLOGY), rabbit anti-phospho-PTEN (Ser370) polyclonal antibody 07-889), rabbit anti-phospho-PTEN (Ser385) polyclonal antibody (07-890) (Upstate (Millipore)), and mouse anti-SHIP1 (P1C1) monoclonal antibody (sc-8425) were used. In addition, as a secondary antibody, horse radish peroxidase (HRP) labeled anti-mouse IgG antibody (NA931V) (GE Healthcare), HRP labeled anti-rabbit IgG antibody (P0399) (DakoCytomation), AlexaFluor 546 labeled anti-goat anti-mouse IgG (heavy chain, light chain) antibody, and AlexaFluor 488 labeled goat anti-rabbit IgG (heavy chain, light chain) antibody (invitrogen (Molecular Probe)) were used.

(2) Western Blot Method

After collection of $1 \times 10^6$ cells, the cells were washed with phosphate buffered saline (10 mM phosphoric acid buffer solution, 120 mM NaCl, 2.7 mM KCl, pH 7.6) (PBS), and 150 μl of 1×SDS sample buffer solution (62.5 mM Tris-HCl (pH 6.8), 2% SDS, 10% glycerol, 50 mM DTT, 0.01% bromophenol blue) was added to lyse the cells. The lysate was boiled at 95° C. for 5 minutes, and a sample equivalent to $8 \times 10^4$ cells/lane was applied to 10% polyacrylamide gel (acrylamide:bisacrylamide=36.5:1) electrophoresis. The electrophoresis was carried out using Mini-PROTEAN 3 Cell (Bio-Rad) at a constant voltage of 100V for 2 hours. The gel was transferred to PVDF membranes (Millipore) by using Mini Trans-Blot Cell (Bio-Rad) (400 mA/3 hours), and the transferred membranes were subjected to the blocking reaction with Tris-buffered saline/Tween 20 (TBS/T) buffer solution (150 mM NaCl, 10 mM Tris-HCl (pH 7.4), 0.1% Tween 20) supplemented with 1% bovine serum albumin (BSA) at room temperature for 2 hours. Using a primary antibody solution diluted 2000-fold with Can Get Signal® Solution 1 (TOYOBO), the membranes were incubated at 4° C. overnight, and washed three times with TBS/T buffer solution for 5 minutes. Further, the membranes were incubated with a 1:3000 dilution of secondary antibody in Can Get Signal®

Solution 2 (TOYOBO) at room temperature for one hour, and washed three times afterwards with TBS/T buffer solution for 5 minutes. After washing, chemiluminescence was emitted with a Lumi light$^{PLUS}$ Western blotting kit (Roche Applied Science), and image analysis was performed by a Luminoimage Analyzer LAS-3000 (Fujifilm).

Using T cell acute leukemia (T-ALL) cell lines (Jurkat, MOLT4, MKB1, KAWAI), HTLV-1 infected cell lines (HUT102, MT2), and ATL cell lines (ED, KOB, KK1, SO4, Su9T-01, S1T), the expressions of NDRG2, PTEN, and AKT proteins were analyzed by Western blot method [FIG. 7(A)]. As a result, the expression of NDRG2 protein was found in the T-ALL cell lines (Jurkat, MOLT4, MKB1, KAWAI), but a significant decreased expression of NDRG2 was found in the HTLV-1 infected cell lines and ATL cell lines. The expression of PTEN protein was recognized in the T-ALL cell lines except for Jurkat cell line, but a decreased expression of PTEN protein was recognized in the HTLV-1 infected cells and the ATL cell lines. On the other hand, phosphorylation modification of PTEN is promoted in the HTLV-1 infected cells and ATL cell lines, and synchronous to this, promotion of phosphorylation modification of AKT was also observed. Point mutation of PTEN gene was recognized in the Jurkat cell line, and thus it was considered that loss of PTEN protein expression and promotion of AKT phosphorylation took place by such a point mutation.

The expressions of NDRG2, PTEN, and AKT proteins were analyzed by Western blot method using CD4+ T cells derived from healthy subjects, and ATL cells derived from patients with acute type ATL. Significant decreased expressions of NDRG2 protein and PTEN protein were found in the ATL cells derived from acute type ATL patients compared to CD4+ T cells derived from healthy subjects as the control. Promotion of phosphorylation modification of AKT was also found in all cases of acute type ATL patients [FIG. 7(B)].

Using the following cancer cell lines except for ATL, the expressions of NDRG2, PTEN, and AKT proteins were analyzed by Western blot method.

Pancreatic cancer (PC) cell lines (KLM-1, PK9, PK45P); hepatocyte cancer (HCC) cell lines (HepG2, HuH-7, HLF); gastric cancer (GC) cell lines (MKN28, MKN45, KATO-III); neuroblastoma (NB) cell lines (NH-6, NH-12); lung cancer cell lines (A549); brain tumor cell lines (A172); breast cancer cell lines (SK-BR-3); colon cancer cell lines (COLO205); uterine cancer cell lines (HeLa); ovarian cancer cell lines (SKOV3); prostate cancer cell lines (PC3); and oral cavity squamous cell cancer cell lines (HO-1-u-1).

As a result, a significant decreased expression of each of NDRG2 and PTEN was found in solid cancer cell lines except for the neuroblastoma cell lines and lung cancer cell lines. On the other hand, phosphorylation modification of PTEN is also promoted in the solid cancer cell lines, and synchronous to this, promotion of the phosphorylation modification of AKT was also found (FIG. 8(A), FIG. 8(B)).

Example 2

Effect of NDRG2 Protein on PTEN Dephosphorylation

1. Binding of NDRG2 Protein to PTEN Protein
(1) Preparation of Samples

Cells were washed with PBS buffer solution, and then lysed by the addition of 500 μl of RIPA buffer solution (50 mM Tris-HCl (pH 8.0), 150 mM NaCl, 1 mM EDTA (pH8.0), 2% Triton X-100, 0.1% SDS). After addition of 1 μg of a specific antibody, the lysate was incubated at 4° C. overnight, washed with TBST buffer solution, and 50 μl of ProteinG Sepharose TM4 fast flow (GE Healthcare) was added, followed by incubation at 4° C. for one hour. Then, the reaction product was washed with PBS buffer solution, added with 50 μl of SDS Sample Buffer Solution, boiled at 95° C. for 5 minutes, and used for Western blot analysis.

(2) Western Blot Analysis

A FLAG-NDRG2 expression vector or a GFP-PTEN expression vector was introduced into 293T cells alone or at the same time, and the cells were cultured 48 hours. After preparing a cell extract, an immunoprecipitation with anti-FLAG antibody was carried out. The expression of the introduced gene was confirmed by the Western blot method using an anti-FLAG antibody and an anti-PTEN antibody [FIG. 9(A), panel (A)]. When the immunoprecipitated products were subjected to Western blot with an anti-PTEN antibody, a band corresponding to PTEN was detected [FIG. 9(A), panel B], revealing that PTEN was bound to NDRG2. In the immunoprecipitation using the anti-PTEN antibody as a confirmation experiment, a similar binding of PTEN to NDRG2 was found (FIG. 9(A), panel C).

(3) Immunoprecipitation Test

In order to examine whether endogenous PTEN and NDRG2 are present in a binding state, an immunoprecipitation test was performed using an extract of MOLT4 cells. Since PTEN was detected by Western blot of anti-NDRG2 antibody immunoprecipitation products using an anti-PTEN antibody, it was found that both of NDRG2 and PTEN were endogenously interacting with each other. On the contrary, a similar result was obtained in a Western blot experiment on the immunoprecipitation products using an anti-PTEN antibody (FIG. 9(B)).

(4) Immunostaining Test

Figure 10:
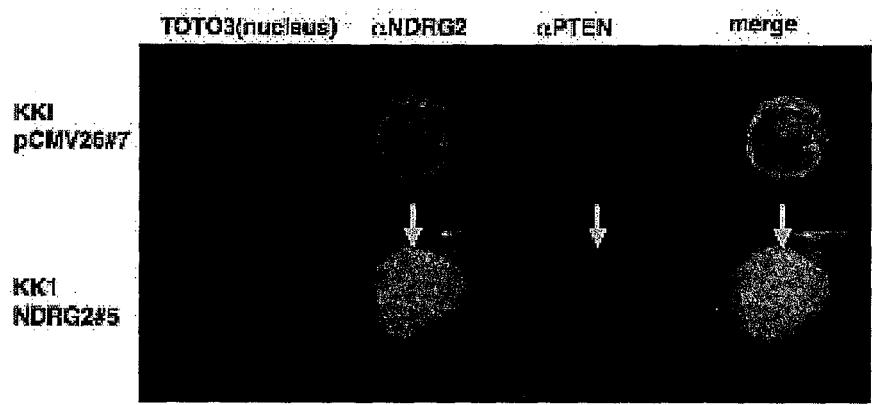
FIG. 10 is a photograph of antibody fluorescent staining, which shows the localization of NDRG2 and PTEN proteins in KK1-ATL cells.

An examination was performed whether the localization of NDRG2 protein in the cell was identical with that of PTEN protein in the cell by an immunofluorescence staining. As a result of detection of NDRG2 with Alexa fluor 488 (green) and PTEN with Alexa fluor 546 (red) in the ATL cell line KK1, it was found that NDRG2 and PTEN proteins were colocalized regardless of the expression level of NDRG2. In the KK1 cells with decreased expression of NDRG2, NDRG2 and PTEN exist in the cytoplasm, and showed the identical localization. When NDRG2 was forcibly expressed in the cells, NDRG2 as well as PTEN were changed to localize in the nucleus at the same time, and the nuclear shape was round (FIG. 10).

2. Dephosphorylation Effect for PTEN by Purified NDRG2 Protein (1) Production of GST (Glutathione S-Transferase)-NDRG2 Fusion Protein The NDRG2 coding region was amplified with use of NDRG2/pCMV26 as a template, and GST-NDRG2-5' BamHI primer (5'-CCCAAGCTTATGGCGGAGCTGCAG-GAGGTGC-3' (SEQ ID NO: 27 in the Sequence Listing)) and NDRG2-3'-EcoRI primer (5'-GCGAATTCTCAACAG-GAGACCTCCATG-3' (SEQ ID NO: 28 in the Sequence Listing)). PCR was performed for 25 cycles (one thermal cycle: 98° C., 10 seconds, 55° C., 5 seconds, 72° C., 15 seconds) using Prime star MAX DNA polymerase kit (TAKARA). The obtained PCR product was inserted into the BamHI site and EcoRI site of pGEX-6P-1 (GE Healthcare) (NDRG2/pGEX-6P-1). The NDRG2/pGEX-6P-1 was transformed into E. coli BL21DE3, and induced to express a fusion protein under the conditions of 1 mM IPTG, 30° C., 3 hours. The E. coli cells were collected by centrifuge, suspended in TBST buffer solution, and disrupted by ultrasonic waves. After centrifugation, the supernatant was collected, and Glutathione Sepharose TM 4B substituted with TBST (GE Healthcare) was added. The mixture was allowed to react at 4° C. for one hour, and GST-NDRG2 protein was eluted with an elution buffer solution (50 mM Tris-HCl (pH8.0), 10 mM glutathione).

(2) pNPP (p-Nitrophenyl Phosphate) Assay

The GST-NDRG2 protein (10 ng to 250 ng) was added to a reaction solution (pH 5.0) consisting of 100 mM sodium acetate, 0.8 mM DTT, and 10 mM pNPP, and the mixture was allowed to react at 30° C. for 10 minutes. After addition of 500 µl of 5 M NaGH, the reaction was stopped and OD 410 nm of the absorption wavelength for pNP (p-Nitrophenol) was measured. A standard curve was prepared at a concentration of 0.2 to 1.6 nmol of pNP, and an enzyme activity was determined by converting the absorbance into the concentration of pNP.

Figure 11A:
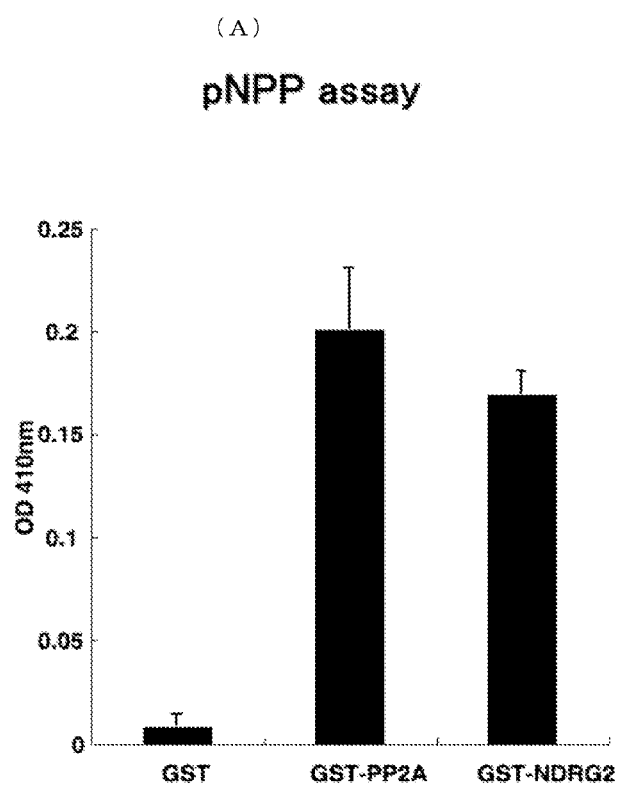
FIG. 11 shows the investigation of enzymatic properties of NDRG2, wherein (A) is a graph showing the properties as a phosphatase by pNPP assay, and (B) is graphs and a table showing enzymatic studies of phosphatase inhibitors.

As a result, the production of pNP was not observed in the GST protein, but the production of pNP was observed as expected in a reaction using PP2A known as a phosphatase (FIG. 11(A)). It was found that NDRG2 possessed a property as a phosphatase because the GST-NDRG2 protein promoted the production of pNP.

(3) Enzymatic Study of NDRG2 by Phosphatase Inhibitors

A phosphatase inhibitor was used to examine whether NDRG2 is a phosphatase. Examples of the phosphatase inhibitor include sodium fluoride (NaF), sodium pyrophosphate, sodium ortho-vanadate, and Okadaic acid. As a result, enzymatic activity of NDRG2 was inhibited by sodium fluoride (NaF) and sodium pyrophosphate, and its IC50 was 383.4 nM and 5219.3 nM, respectively when the concentration of NDRG2 protein was 25 ng/ul (FIG. 11(B)).

(4) Phosphopeptide Phosphatase Assay (Dephosphorylation System Using Phosphorylated Peptide)

To a reaction solution consisting of 20 mM magnesium acetate, 300 µg/ml BSA, 30 µM EDTA, 0.03% β-mercaptoethanol, and 25 ng/ml GST-NDRG2 were added 10 ng to 500 ng of various phosphorylated PTEN peptides (Non-phospho PTEN (373-EPDHYRYSDTTDSDPENE-382 (SEQ ID NO: 29 in the Sequence Listing)), pSer380 PTEN (EPDHYRY pSDTTDSDPENE), pThr382 PTEN (EPDHYRYSD pTTDSDPENE), pThr383 PTEN (EPDHYRYSDT pTDSDPENE), pThr382/pThr 383 PTEN (EPDHYRYSD pTpTDSDPENE), pSer380/pThr382/pThr 383 PTEN (EPDHYRYpSDpTpTDSDPENE), and the mixture was allowed to react at 30° C. for 10 minutes. Then, 140 µl of BIOMOL GREEN (BIOMOL) and 530 µl of distilled water were added thereto, and the OD620 nm was measured. A standard curve was prepared by BIOMOL GREEN reaction using a 0.2 nmol to 1.6 nmol solution of free phosphoric acid, and Vmax and Km values were determined in terms of phosphoric acid group concentration from the absorbance.

Figure 12:
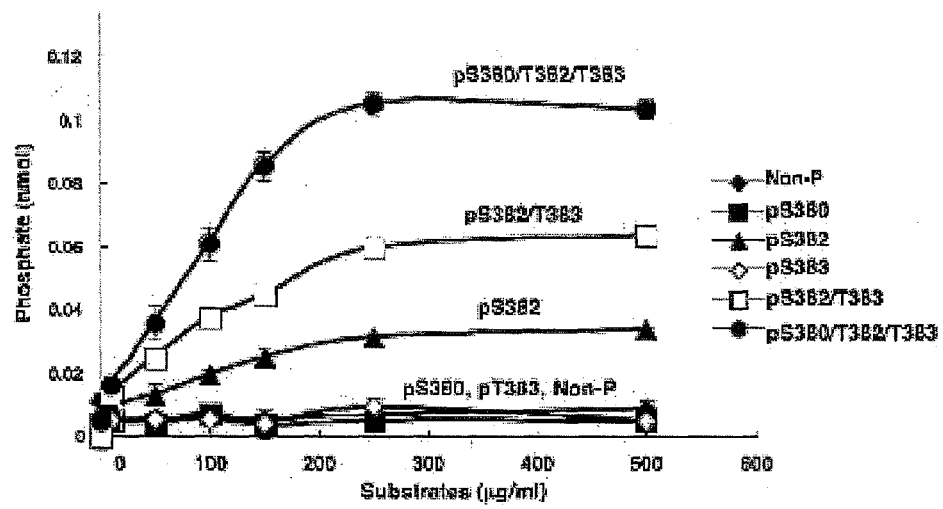
FIG. 12(A) is a graph showing a phosphatase specificity to PTEN by NDRG2 protein, and (B) is a photograph by the Western blot technique showing a phosphatase specificity to PTEN by NDRG2 protein.
Figure 12:
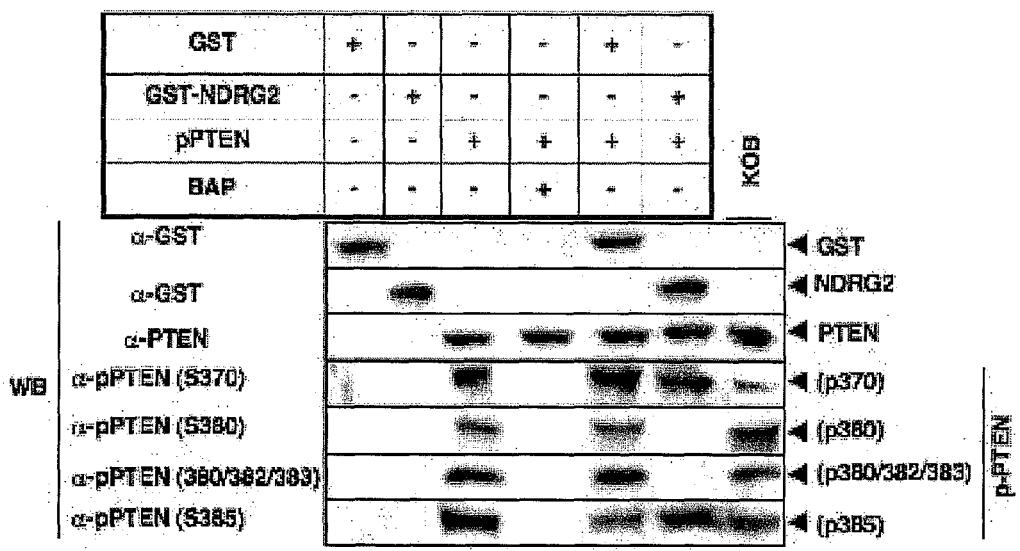

As a result, NDRG2 showed a dephosphorylation activity against the peptide including the phosphorylation at Thr382 of PTEN (FIG. 12(A)). An indirect dephosphorylation effect on Ser380 and Thr383 by NDRG2 was shown because an increase in the production level of the phosphoric acid groups in the Thr382/Thr383 peptide and Ser380/Thr382/Thr383 peptide was recognized compared to the phosphorylation of Thr382 alone.

(5) Dephosphorylation Test of PTEN by NDRG2

Purification of PTEN Protein from ATL Cell Lines

ATL cell line Su9T-01 of $1 \times 10^7$ cells were transfected with 20 µg of PTEN/pCMV26 expression vector by electroporation. On day 2 after the transfection, the cells were collected and 500 µl of RIPA buffer solution was added to prepare a cell extract solution. After addition of 50 µl of Anti-FLAG M2 affinity Gel (SIGMA), the mixture was incubated at 4° C. overnight. The reaction solution was washed with PBS buffer solution, and eluted with 3×FLAG peptide (100 µg/ml).

In Vitro Dephosphorylation Experiment

A reaction solution composed of 25 ng of GST or GST-NDRG2 or one unit of bacterial alkaline phosphatase (BAP) (TAKARA) was reacted with a reaction solution consisting of 20 mM magnesium acetate, 300 µg/mL BSA, 30 µM EDTA, 0.03% β-mercaptoethanol, and 10 ng/ml FLAG-PTEN at 30° C. for 30 minutes. Phosphorylation state of PTEN was analyzed by the Western blot method using anti-PTEN antibodies specific to each phosphorylation.

As a result, dephosphorylation of PTEN was not recognized in the GST protein, but dephosphorylation effects were recognized in BAP used as a positive control, and in GST-NDRG2 [FIG. 12(B)]. In particular, by using an endogenous PTEN protein, it was proved that NDRG2 has a function to dephosphorylate the Thr382 residue.

(6) Dot Plot Phosphatase Assay (Dephosphorylation Test for Phosphorylated Peptide of PTEN by NDRG2)

Various phosphorylated PTEN peptides were added to a reaction solution consisting of 20 mM magnesium acetate, 300 mg/ml BSA, 30 mM EDTA, 0.03% β-mercaptoethanol, and 25 ng/ml GST-NDRG2 protein, and allowed to react at 30° C. for 10 minutes. The reaction solution was dropwise added to PVDF membranes, dried in the air, and the membranes were blocked in TBS/T buffer solution supplemented with 1% BSA or 5% skim milk at room temperature for 2 hours. The membranes were incubated at 4° C. overnight by using a 1:2000 primary antibody in Can Get Signal® Solution 1 (TOYOBO), and washed with TBS/T buffer solution for 5 minutes, 3 times. Subsequently, the membranes were allowed to react with a secondary antibody which had been diluted 3000-fold in Can Get Signal® Solution 2 (TOYOBO) at room temperature for one hour, and then washed with TBS/T buffer solution for 5 minutes, 3 times. Chemiluminescence was emitted with a Lumi light$^{PLUS}$ Western blotting kit (Roche Applied Science), and image analysis was performed by a Luminoimage Analyzer LAS-3000 (Fujifilm).

Figure 13:
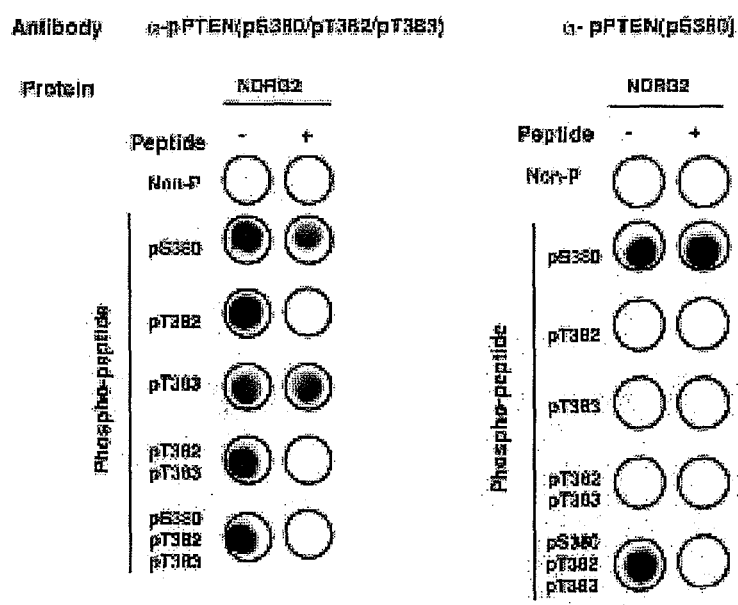
FIG. 13(A) is a photograph showing the result of dephosphorylation of PTEN phosphorylated peptide by NDRG2 according to DOTBLOT method, and (B) is a photograph of the Western blot technique showing the effect of the activation level of the P13K/AKT signaling pathway by amino acid substitutions in the phosphorylation sites of PTEN protein.
Figure 13:
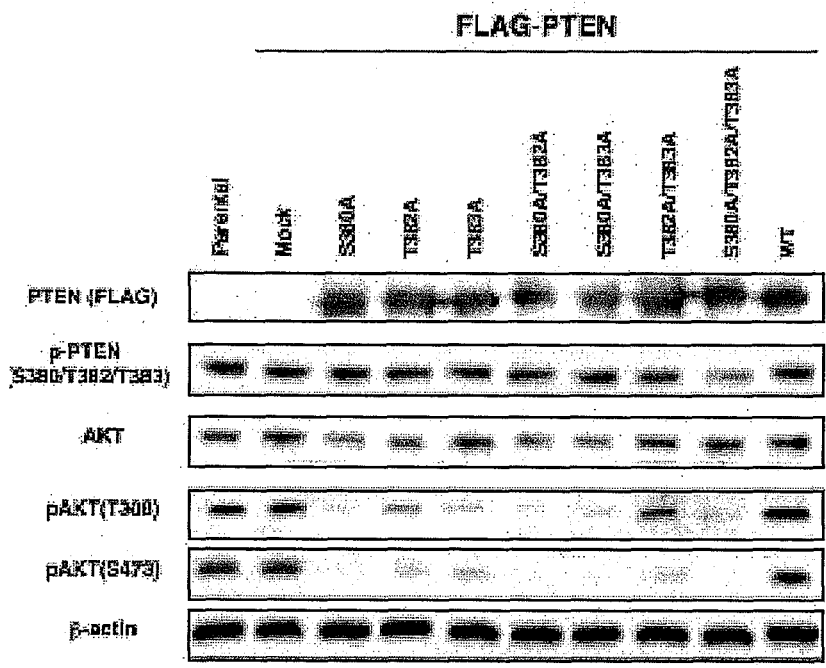

As a result of detection with rabbit anti-Phospho-PTEN (Ser380/Thr382/Thr383) polyclonal antibodies, signals disappeared in the phosphorylated peptides at Thr382, Thr382/Thr383, and Ser380/Thr382/Thr383 by the reaction with NDRG2 protein [FIG. 13(A)]. As a result of detection with rabbit anti-phospho-PTEN (Ser380) polyclonal antibodies, a signal disappeared in the phosphorylated peptide of Ser380/Thr382/Thr383 by the reaction with NDRG2 protein. Thus, this suggested the possibility that NDRG2 dephosphorylated not only Thr382 of PTEN, but also Ser380 and Thr383 at the same time.

(7) Activation Test of P13K/AKT Signaling Pathway by Introduction of Point Mutation to PTEN Protein Construction of Expression Vector for Mutated PTEN Gene For the phosphorylation sites S380, T382, and T383 of PTEN protein, a mutated PTEN expression vector with a point mutation was produced. Mutation introduction PCR was performed using PTEN/pCMV26 as a template, and S380A mutated PTEN primer (ATAGATATGCTGACACC) (SEQ ID NO: 30 in the Sequence Listing), PTEN T382A mutated PTEN primer (ATTCTGACGCCACTGAC) (SEQ ID NO: 31 in the Sequence Listing), PTEN T383A mutated PTEN primer (TATAGATATTCTGACACCGCTGACTCT-GAT) (SEQ ID NO: 32 in the Sequence Listing), PTEN S380A, T382 mutated PTEN primer (TAAGATATGCT-GACGCCACTGAC) (SEQ ID NO: 33 in the Sequence Listing), PTEN S380A, T383 mutated PTEN primer (TATA-GATATGCTGACACCGCTGACTC) (SEQ ID NO: 34 in the Sequence Listing), PTEN T382A, T383 mutated PTEN primer (TATTCTGACGCCGCTGACTCTG) (SEQ ID NO:

35 in the Sequence Listing), and PTEN S380A, T382A, T383 mutated PTEN primer (TATAGATATGCTGACGCCGCT-GACTCTG) (SEQ ID NO: 36 in the Sequence Listing). PCR was performed for 35 cycles (one thermal cycle: 98° C., 10 seconds; 55° C., 5 seconds; and 72° C., 90 seconds) using Primestar Max DNA polymerase (TAKARA), and mutation introduction was confirmed by DNA sequencing.

Western Blot Method

The PTEN mutated gene expression vector produced was introduced into HTLV1 infected cell line HUT102 with an Amaxa Nucleofector, and the activation level of the P13K/AKT signaling pathway was investigated by the Western blot method [FIG. 13(B)]. As a result, it was found that the functions of PTEN were recovered because AKT was dephosphorylated if PTEN protein in the absence of phosphorylation at any one point of the three sites of T383, S380, and T382 was present. In other words, it was shown that all of the three sites had to be phosphorylated to reduce the PTEN function.

(8) Cell Proliferation Test

Analysis of Cell Proliferation

At 12 hours after the gene introduction, 100 μl of the cells ($1 \times 10^4$ cells/mL) were cultured in a 96-well plate under various conditions, added with cell counting kit-8 (DOJINDO) every 24 hours, and the absorbance at 420 nm was measured to analyze the cell proliferation ability. Stationary culture of the cells was performed under the conditions of 37° C. and 5% $CO_2$.

Figure 14:
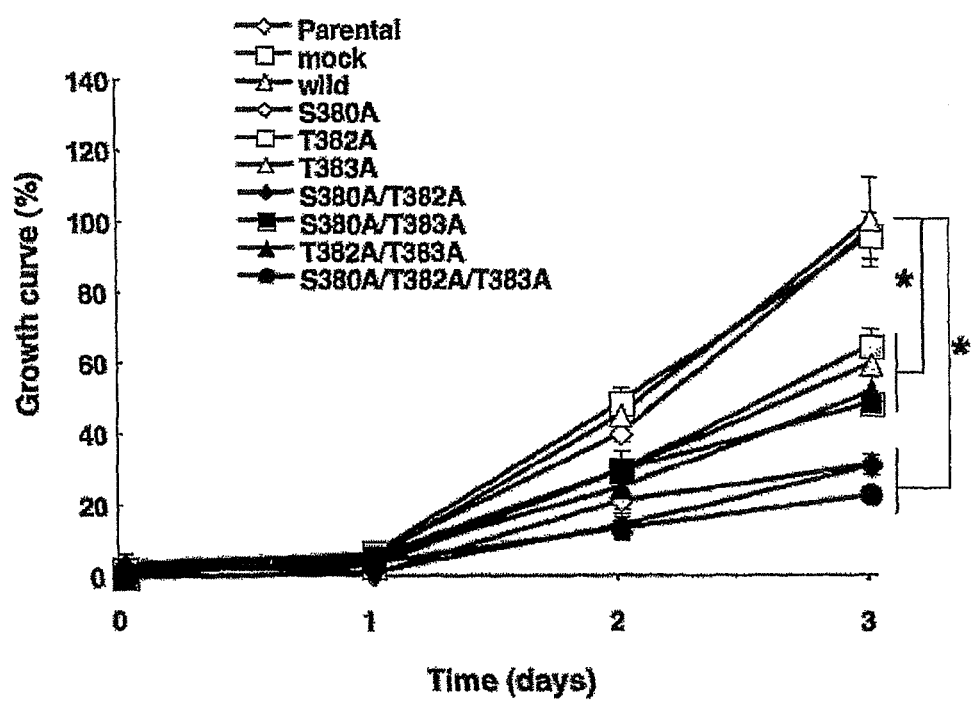
FIG. 14 is a graph showing promoted cell proliferation ability by the dephosphorylation of PTEN.

As a result, cell proliferation was significantly suppressed by the existence of the mutated PTEN protein (FIG. 14). There was a difference in the cell proliferation ability depending on the sites of mutation, and the most suppression for the cell proliferation ability was observed in the PTEN protein which had mutations at all three sites of S380, T382, and T383.

Example 3

Therapy Test of ATL by NDRG2

1. Construction of NDRG2 Gene Expression Vector

NDRG2 coding region was amplified by using MOLT4 cDNA as a template, and NDRG2-5'-HindIII primer (5'-CCCAAGCTTATGGCGGAGCTGCAGGAGGTGC-3' (SEQ ID NO: 37 in the Sequence Listing)) and NDRG2-3'-EcoRI primer (5'-GCGAATTCTCAACAGGAGACCTC-CATG-3' (SEQ ID NO: 38 in the Sequence Listing). PCR was performed for 30 cycles (one thermal cycle: 98° C., 10 seconds; 55° C., 30 seconds; and 72° C., 75 seconds) using Ex Taq DNA polymerase (TAKARA). The resulting PCR product was introduced into the sites of HindIII and EcoRI, downstream of FLAG-tag in pCMV26 (SIGMA ALDRICH) (NDRG2/pCMV26). The isolated NDRG2 cDNA was found to be the type B (NM_016250) by DNA sequencing.

2. Production of ATL Cell Lines Stably Expressing NDRG2

ATL cell lines KK1 and Su9T-01 cells ($1 \times 10^7$ cells) were transfected with 20 μg of DNA (NDRG2/pCMV26 or pCMV26) by electroporation. The electroporation was performed by using GENE PLUSER II (Bio-Rad) under the conditions of 220V and 950 μF. On day 2 after the transfection, G418 (GIBCO) was added to the culture solution at a concentration of 800 μg/ml, and selection with G418 resistance over one week was carried out to obtain ATL cell clones stably transfected with NDRG2 gene. After establishment of the stable expression cell lines, G418 was added to a culture medium at a concentration of 200 μg/ml, and passage culture was performed. The cell lines produced are KK1 cell lines transfected with pCMV26 (KK1/pCMV26-#7, KK1/pCMV26-#11), KK1 cell lines transfected with NDRG2/pCMV26 expression vector (KK1/NDRG2-#5, KK1/NDRG2-#6), Su9T 01-cell lines transfected with pCMV26 (Su9T-01/pCMV26-#2, Su9T-01/pCMV26-#4), and Su9T-01 cell lines transfected with NDRG2/pCMV26 expression vector (Su9T-01/NDRG2-#5, Su9T-01/NDRG2-#6).

3. Western Blot Analysis

Figure 15A:
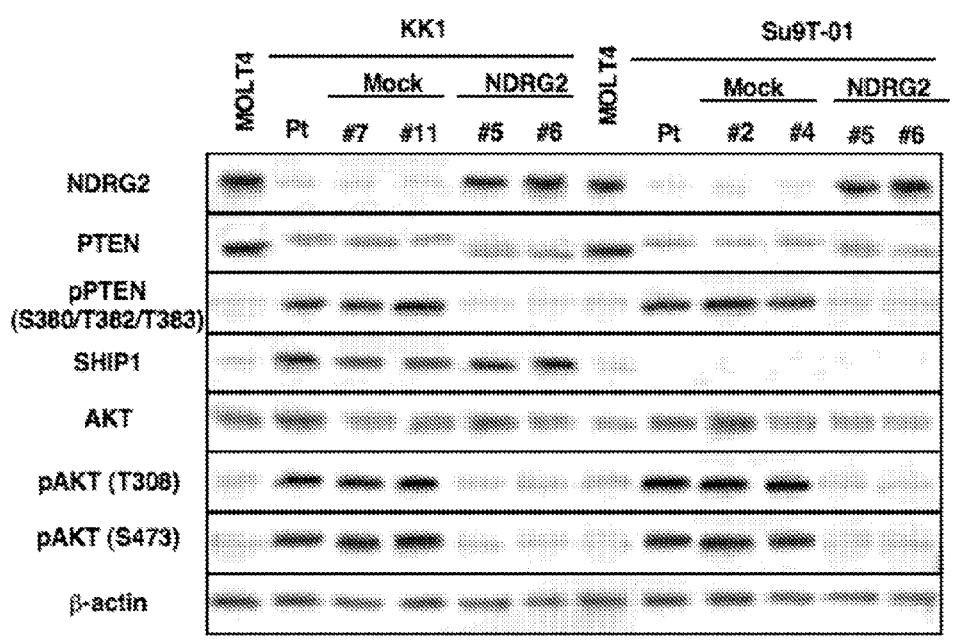
FIG. 15 shows the effect for a high expression of NDRG2 in ATL cell lines, wherein (A) is a photograph by the Western blot technique showing the activity inhibition in the P13K/AKT signaling pathway, and (B) is graphs showing the decrease in cell proliferation ability.

Using the established ATL cell lines stably expressing NDRG2, the expressions of NDRG2, PTEN, and AKT proteins were analyzed by the Western blot method (FIG. 15(A)). A remarkable decrease in the expression of NDRG2 protein was recognized in the parent cell line (Pt) and the cell line (MOCK) transfected with pCMV26 as compared with MOLT4, but the expression of NDRG2 protein was recognized in a cell line (NDRG2) transfected with NDRG2/pCMV26. There was no significant difference in the expression level of PTEN and AKT proteins between the control cell line and the NDRG2/pCMV26 cell line, but decrease in the phosphorylated PTEN protein as well as in the phosphorylated AKT protein was recognized in the ATL cell line stably expressing NDRG2.

4. Analysis of Cell Proliferation

Cells were seeded at a density of $1 \times 10^5$ cells/ml, and the viable cells were counted by trypan blue staining at 24-hour intervals. Dilution (1/10-fold) passage was performed every 2 days, and culture was performed for 2 weeks. The cells were subjected to a stationary culture under the conditions of 37° C. and 5% $CO_2$. A significant decrease in the cell proliferation ability was recognized in the ATL cell lines stably expressing NDRG2 (KK1/NDRG2, Su9T-01/NDRG2) compared to the parent cell line and the cell line transfected with pCMV26 (FIG. 15(B)).

5. In Vivo Test of Tumorigenicity

The Su9T-01/pCMV26-#4 cell line or Su9T-01/NDRG2-#6 cell line ($1 \times 10^7$ cells) was intravenously or intraperitoneally administered to immunodeficient mice (NOD/Shi-scid, IL-2R$\gamma^{null}$ (NOG)). As a result, in the ATL control cell transplantation group with reduced NDRG2 (black circles), all of the 10 animals died in about 160 days, and 50% survival period was 67 days, while in the ATL cell transplantation group with forced expression of NDRG2 (open circles), all of the 10 animals died in about 308 days, and 50% survival period was 217 days, which showed a significant prolonged survival ($p<0.01$) (FIG. 16(A)).

6. Immunofluorescence Staining Test

The cells were washed with PBS, immobilized with a 4% paraformaldehyde solution, subjected to transmission processing with 0.1% Triton-X100/PBS, and blocked using TBS/T buffer solution supplemented with 1% BSA. The cells were washed three times with TBS/T, and incubated with a primary antibody solution (diluted 400-fold in TBS/T supplemented with 1% BSA) at room temperature for 2 hours. After three times washing with TBS/T buffer solution, AlexaFluor 488 fluorescence-labeled goat anti-rabbit IgG (diluted 1000-fold), AlexaFluor 546-labeled anti-goat anti-mouse IgG (diluted 1000-fold), and DAPI (SIGMA ALDORICH) (0.2 μg/ml) were added thereto, and the mixture was incubated at room temperature for one hour under the light shielding condition. After three times washing with TBS/T buffer solution, a fluorescent mounting medium (DAKO) was added for the mounting of the reaction product, and the fluorescence was observed using an inverted epi-fluorescent microscope (HAL100) (Carl Zeiss), or an inverted confocal laser scanning microscope (DMIRE2) (Leica).

Figure 16:
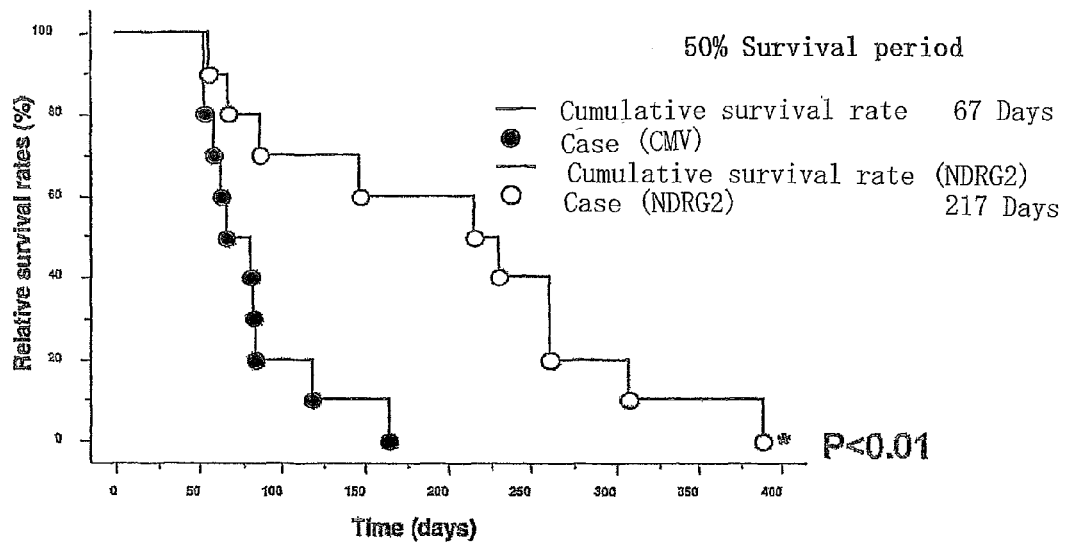
FIG. 16(A) is a graph showing the duration of survival of transplanted cells in NOG mice into which ATL cell lines highly expressing NDRG2 have been transplanted, and (B) is a photograph showing the recover of a transcription factor FOXO1 protein in ATL cell lines highly expressing NDRG2.
Figure 16:
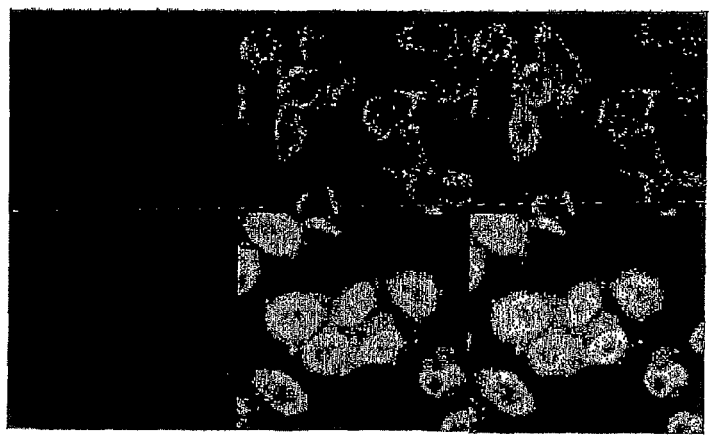

In order to further verify an inhibitory effect on the P13K/AKT signaling pathway by NDRG2, localization of FOXO protein that was a target molecule of the phosphorylated AKT was analyzed by immunofluorescence staining (FIG. 16 (B)). It was found that in the ATL cell line (KK1/pCMV26-#11) as a control, FOXO1/4 protein was localized in the cytoplasm with the activation of AKT, but the FOXO1/4 protein was localized in the nucleus of the ATL cell line expressing NDRG2 (KK1/NDRG2-#5).

Abnormal flower-like nuclei are known to be characteristic of ATL cells. It was recognized that cells with a broad bean-like notch and deformation in the nucleus of KK1/pCMV26-#11 tended to increase. Thus, the nuclear shape was investigated in more detail (FIG. 17(A)). The degree of nuclear deformation was divided into four groups, and the cells were subjected to DAPI staining, and classified twice (100 cells each) by fluorescence microscopy. Nuclear deformation was observed in ATL cell lines (KK1/pCMV26-#7, Su9T-01/pCMV26-#4) (KK1; 78%, Su9T-01; 68%) in control ATL cell lines KK1 and Su9T-01, but cells with round nuclear shape close to normal cells in the cell lines stably expressing NDRG2 were increased from 22% to 93% in the KK1 cells and from 32% to 53% in the Su9T-01 cells. Therefore, the decreased expression of NDRG2 gene was suggested to be involved in the formation of flower-like nuclei.

Immunofluorescence staining using an anti-α-tublin antibody revealed that promotion of tubulin polymerization was suppressed in the ATL cell lines expressing NDRG2 (FIG. 17(B)).

Example 4

Therapy Test of Pancreatic Cancer with NDRG2

1. Production of Pancreatic Cancer Cell Lines Stably Expressing NDRG2

One μg of NDRG2/pCMV26 or pCMV26 plasmid and 3 μl of hilymax (DOJINDO) were added to 100 μl of RPMI 1640, and allowed to react at room temperature for 15 minutes, thereby to introduce the gene into two pancreatic cancer cell lines (KLM-1, PK45-P). Two days after introduction, G418 was added to the culture solution at a concentration of 600 μg/ml, and selection with G418 resistance over two weeks was carried out to obtain pancreatic cancer cell clones stably transfected with NDRG2 gene. After establishment of stable expression cell lines, G418 was added to each culture medium at a concentration of 200 μg/ml and then passage culture was performed. The generated cell lines include KLM-1 cell lines transfected with pCMV26-cell (KLM-1/pCMV26-#1, KLM-1/pCMV26-#2), KLM-1 cell lines transfected with NDRG2/pCMV26 expression vector (KLM-1/NDRG2-#1, KLM-1/NDRG2-#2), PK45-P cell lines transfected with pCMV26 (PK45-P/pCMV26-#1, PK45-P/pCMV26-#2), and Su9T-01 cell lines transfected with NDRG2/pCMV26 expression vector (PK45-P/NDRG2-#1, PK45-P/NDRG2-#2).

2. Western Blot Analysis

Figure 18:
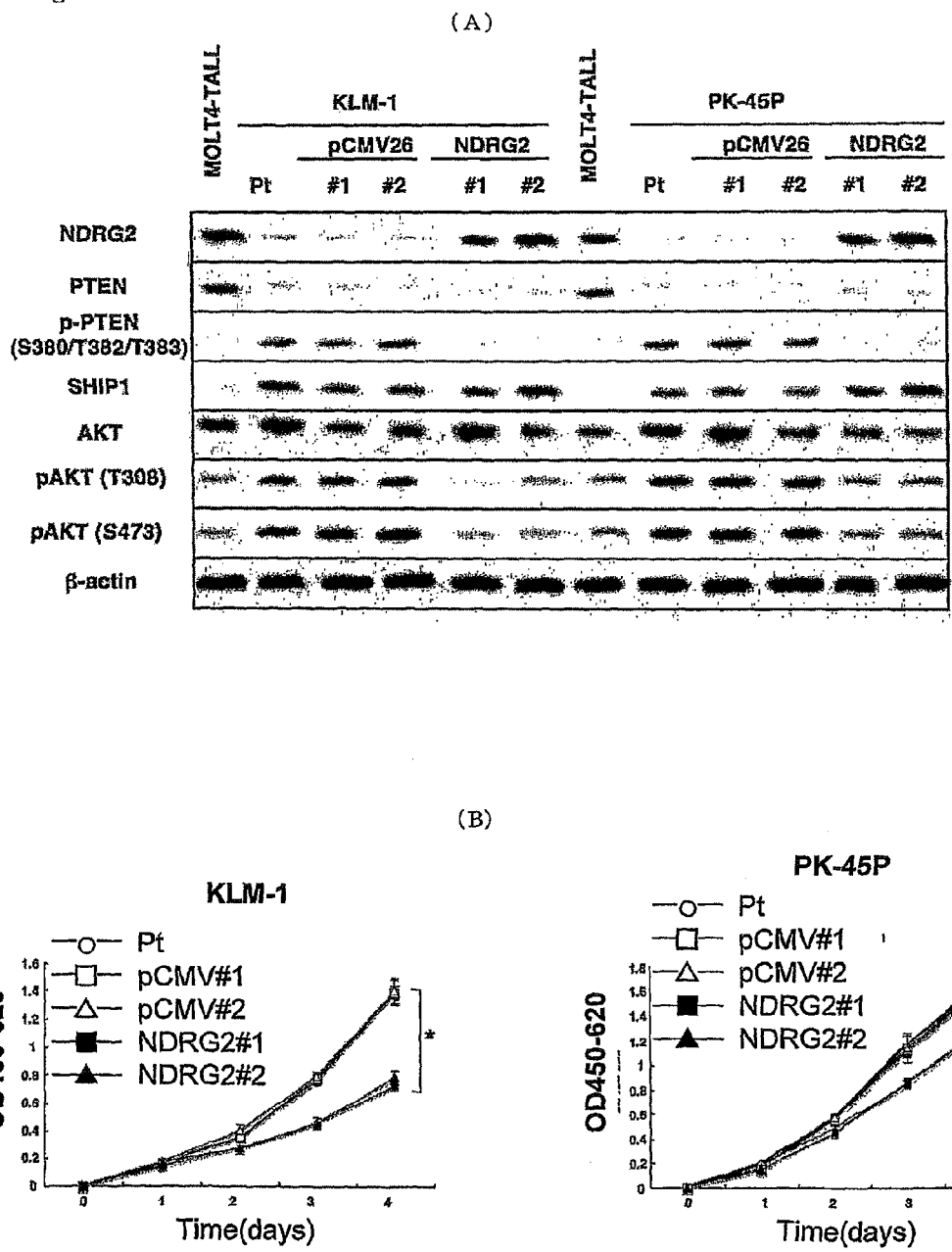
FIG. 18 shows the activation of the P13K/AKT signaling pathway by decreased expression of NDRG2, wherein (A) is a photograph by the Western blot technique showing the expression of each protein in pancreatic cancer, and (B) shows graphs indicating the proliferation-inhibitory effects on the same pancreatic cancer by forced expression of NDRG2.

Using the established pancreatic cancer cell lines stably expressing NDRG2, the expressions of NDRG2, PTEN, and AKT proteins were analyzed by the Western blot method (FIG. 18(A)). Like ATL cell lines, a remarkable decrease in the expression of NDRG2 protein was recognized in the parent cell line (Pt) and the cell line transfected with pCMV26 (Mock) as compared with MOLT4, but the expression of NDRG2 protein was recognized in the cell line (NDRG2) transfected with NDRG2/pCMV26. With respect to the expression level of PTEN and AKT proteins, a significant difference was not recognized between the control cell line and the NDRG2/pCMV26 cell line, but promotion of PTEN dephosphorylation as well as AKT dephosphorylation was recognized in the ATL cell lines stably expressing NDRG2.

3. Cell Proliferation Test

One hundred μl of cells ($1 \times 10^5$ cells/ml) were cultured in a 96-well plate, added with cell counting kit-8 (DOJINDO) every 24 hours, and the absorbance at 420 nm was measured to analyze the cell proliferation ability. Stationary culture of the cells was performed under the conditions of 37° C. and 5% $CO_2$. A significant decrease in the cell proliferation ability was observed in the pancreatic cancer cell line stably expressing NDRG2 (KLM-1/NDRG2, PK-45P/NDRG2) compared to the parent cell line and the cell line transfected with pCMV26 (FIG. 18(B)).

Example 5

Prevention Test of Various Cancers by NDRG2

1. Production of T-ALL Cell Lines Suppressing NDRG2 Expression

Using Nucleofector solution V (Amaxa biosystems), NDRG2 siRNA (5'-GGUGGAGAGGGCAUAUGCAtt-3' (SEQ ID NO: 39 in the Sequence Listing)) or Allstars negative control siRNA (QIAGEN) was introduced into $2 \times 10^6$ cells of T-ALL cell lines MOLT4 and KAWAI under the condition of program S-018.

2. Western Blot Analysis

A significant decrease in the expression of NDRG2 protein was observed in cells transfected with NDRG2 siRNA by Western blot analysis compared to its parent cell line (Pt) as a control and cells transfected with negative control siRNA (ANC). In these cells, increase in the phosphorylation of PTEN and promotion in the phosphorylation of AKT were observed (FIG. 19(A)).

3. Cell Proliferation Test

One hundred μl of cells ($1 \times 10^5$ cells/ml) were cultured in a 96-well plate under various conditions, and viable cells were counted with a cell counting kit every 24 hours for 3 days. Stationary culture of the cells was performed under the conditions of 37° C. and 5% $CO_2$. The promotion of cell proliferation was observed in the T-ALL cells suppressing NDRG2 expression compared to the parent cell line (parental) and cells transfected with negative control siRNA (ANC) (FIG. 19 (B)).

The following can be said based on the findings obtained from the above Examples 1 to 5.

PTEN Gene Expression in ATL Cells

Figure 5:
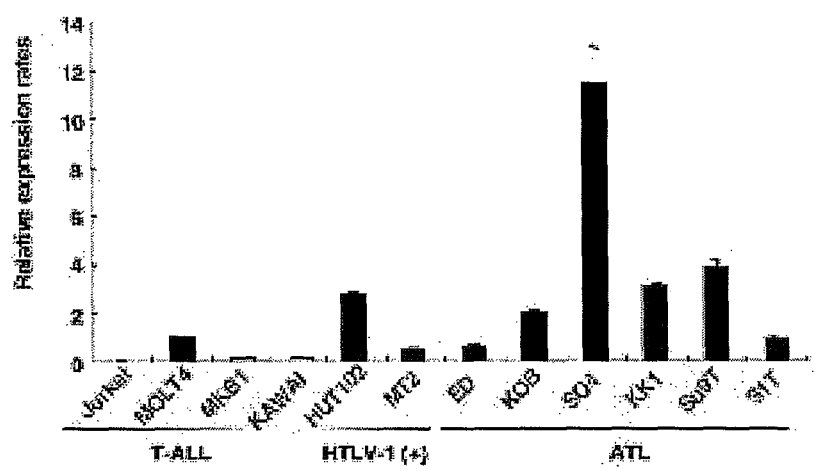
FIG. 5(A) is a graph showing the expression of PTEN gene in T-cell leukemia cell lines.
FIG. 5(B) is a graph showing the expression of PTEN gene in acute-type ATL cells.
Figure 5:
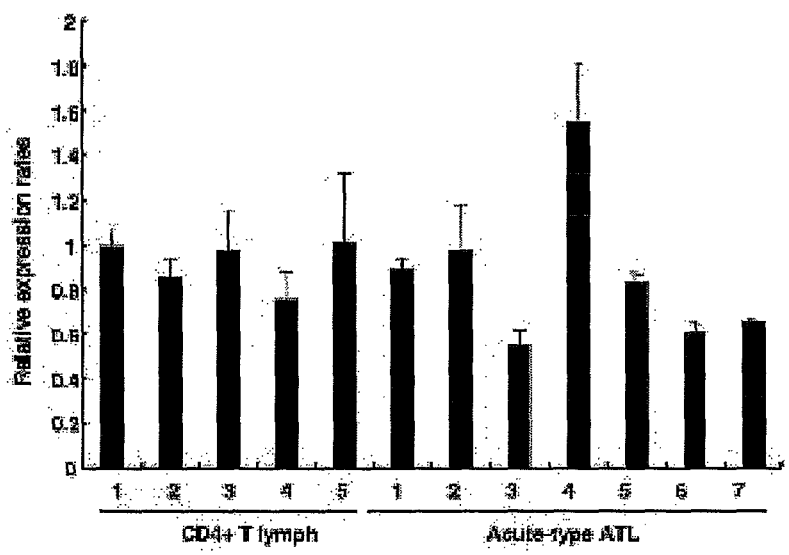

FIG. 5 shows the relationship between ATL and PTEN genes. As shown in FIG. 5(A) of the expression of PTEN gene in T cell leukemia cell lines including ATL, mRNA expression of PTEN is relatively high in the ATL and HTLV-1 infected cell lines compared to other T cell leukemia cell lines. As shown in FIG. 5(B) of the expression of PTEN gene in the cells derived from acute type ATL patients, mRNA expression of PTEN is not decreased compared to normal human peripheral blood CD4+ lymphocytes. Further, as shown in FIG. 6(A), when a point mutation search is performed to determine the nucleotide sequence of each exon by using the cell lines used in the retrieval study of point mutations of PTEN gene and genomic DNA of patient specimens, the point mutation is found in the Jurkat cell line of T-ALL cell lines, but the point mutation is not found in other cell lines.

Relationship Among NDRG2, PTEN, and AKT in ATL Cell Lines

Figure 7:
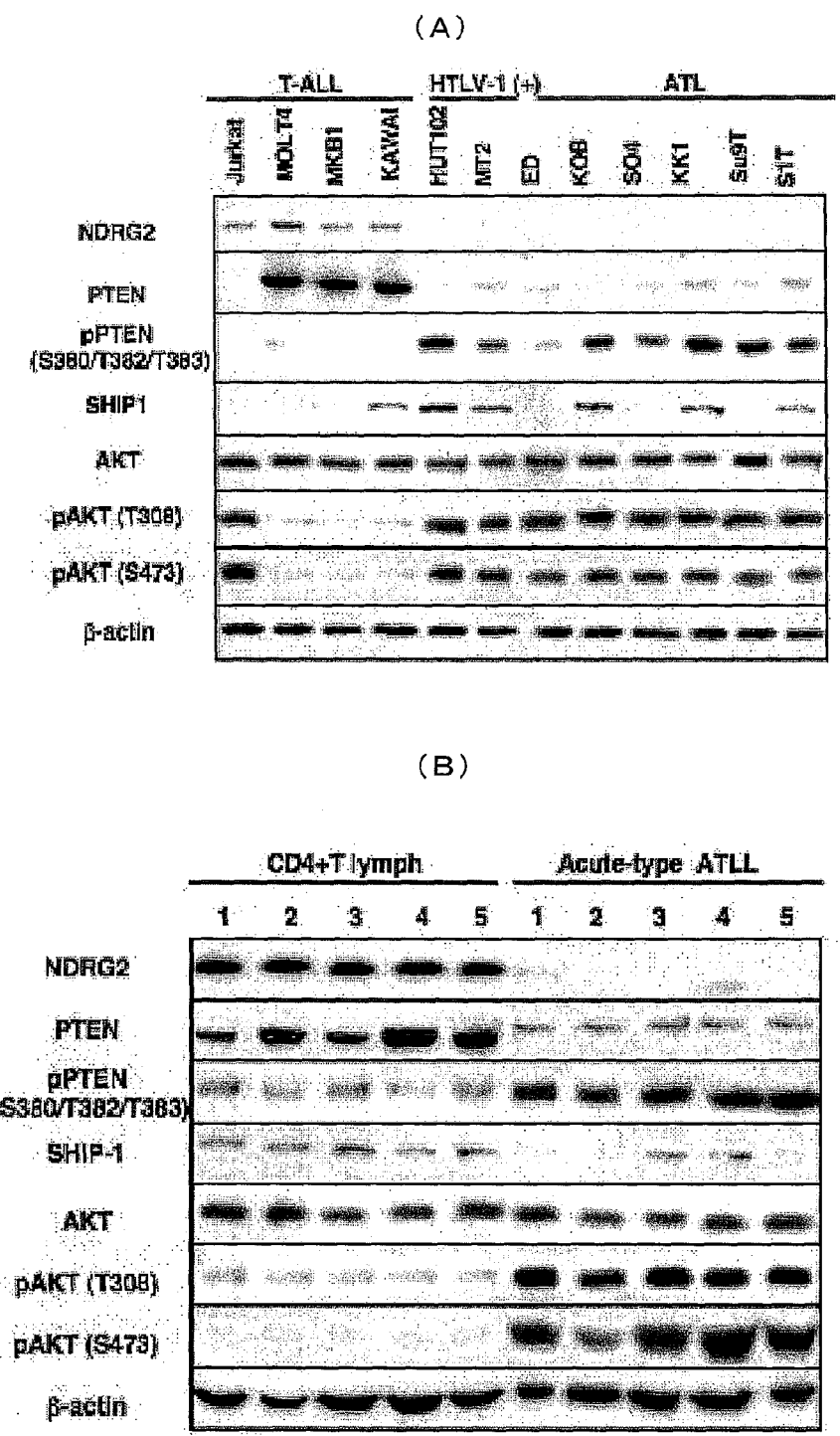
FIG. 7 is a photograph showing the relationship between the decreased in the expression of NDRG2 protein and the activation of the P13K/AKT signaling pathway by the Western blot technique, wherein (A) shows an activated state of the P13K/AKT signaling pathway in ATL cell lines and HTLV-1 cell lines, and (B) shows an activated state of the P13K/AKT signaling pathway in acute ATL cell lines.

According to the findings by the present inventors, phosphorylations at Ser380 Thr382, and Thr383 of PTEN are promoted in the ATL cell lines as shown in FIG. 7. It has been previously suggested that when PTEN is phosphorylated, the original activity of PTEN decreases (Leslie N R, Downes C P. (2004) PTEN function: how normal cells control it and tumour cells lose it. Biochem J. 2004; 382: 1-11. Review). From these, the present inventors observe the behavior of NDRG2, PTEN, and AKT in the ATL cell lines in terms of expression of the corresponding protein by the Western blot method, and as a result, AKT phosphorylation (p-AKT) is promoted in the ATL cell lines with PTEN phosphorylation (p-PTEN) as shown in FIG. 7(A). In addition, as with the decrease in the activity by PTEN phosphorylation, decreased expression of NDRG2 is also recognized. Also in acute type ATL cells, decreased expression of NDRG2 and PTEN proteins and promotion of PTEN and AKT phosphorylations are similarly observed as shown in FIG. 7(B).

Pharmacological Effect of NDRG2 Genes; Effects of PTEN Dephosphorylation

Figure 15B:
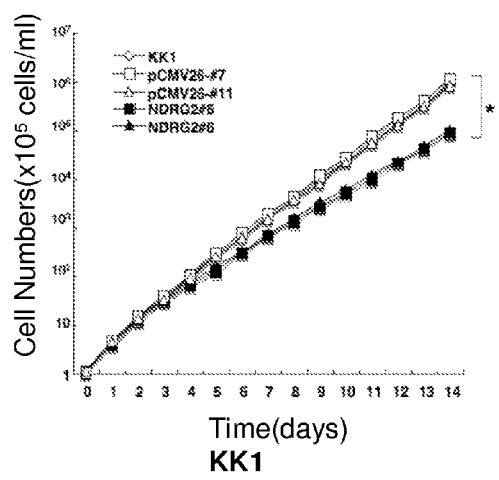
Figure 15B:
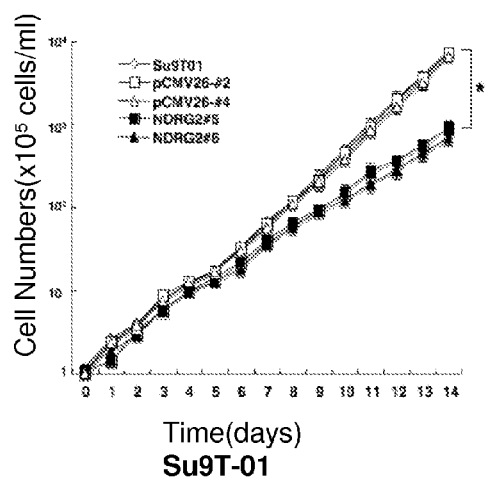

The present inventors introduced NDRG2 gene into ATL cell lines such as KK1 and Su9T-01 so that the relationship between decreased expression of NDRG2 and phosphorylation of PTEN as shown in FIG. 7 was studied, thereby to establish ATL cell lines stably expressing NDRG2, which were analyzed by the similar Western blot method. FIG. 15 shows the results. As shown in FIG. 15(A), when NDRG2 is highly expressed in the ATL cell lines (KK1, Su9T-01) stably expressing NDRG2, phosphorylated PTEN (pPTEN) is decreased and phosphorylated AKT (pAKT) is also decreased. In addition, as shown in FIG. 15(B), high expression of NDRG2 protein in the same ATL cell lines causes a decrease in the ability of cell proliferation. In FIG. 16(A), NDRG2 protein was forcibly expressed in the ATL cell lines, transplanted into NOG mice, and the later follow-up was shown, wherein in the ATL control cell transplantation group with decreased expression of NDRG2 (black circles), 50% survival period was 67 days, while in the ATL cell transplantation group with forced expression of NDRG2 (open circles), 50% survival period was 217 days, which showed a significant prolonged survival. FOXO genes of FIG. 6(D) regulate transcription as a transcription factor in the cell proliferation, metabolism, cell death, and cell repair depending on the basic situation of the cells. In normal conditions, FOXO is present in the nucleus, and performs the transcription activation of genes involved in the inhibition of cell cycle and cell death, but the P13K/AKT signaling pathway is activated when stimulated by the cell proliferation factor. Stimulation of phosphorylated AKT phosphorylates FOXO protein, and it migrates from the nucleus to the cytoplasm, thereby to lose the effect as a transcription factor, and the brakes become ineffective. In the ATL cells, P13K/AKT is in the activated state, and FOXO1 protein is in the cytoplasm. In contrast, in the ATL cells with highly expressed NDRG2, the P13K/AKT signaling pathway is suppressed, the phosphorylation of AKT is suppressed, and FOXO returns to the nucleus, thereby to induce the suppression of cell cycle and cell death. Therefore, cell proliferation is suppressed, suggesting the occurrence of the phenomena of FIGS. 15(B) and 16(A). In FIG. 17(A), when NDRG2 is highly expressed in the ATL cells, the cell nucleus deformation that is the major characteristics of the ATL cells disappears, and cells with round nuclei such as those found in normal peripheral blood lymphocytes are returned. Further, as shown in FIG. 17(B), it is understood that nuclear shape is deformed because tubulin polymerization is promoted in the ATL cell and the nucleus is surrounded by microtubulus. In contrast, in the cell transfected with NDRG2, it is clear that the polymerization disappears, and the nucleus is released from tubulin. These series of dephosphorylation effects for PTEN by NDRG2 shows a sufficient possibility as the therapeutic agent for ATL by NDRG2 in the present invention.

Figure 17:
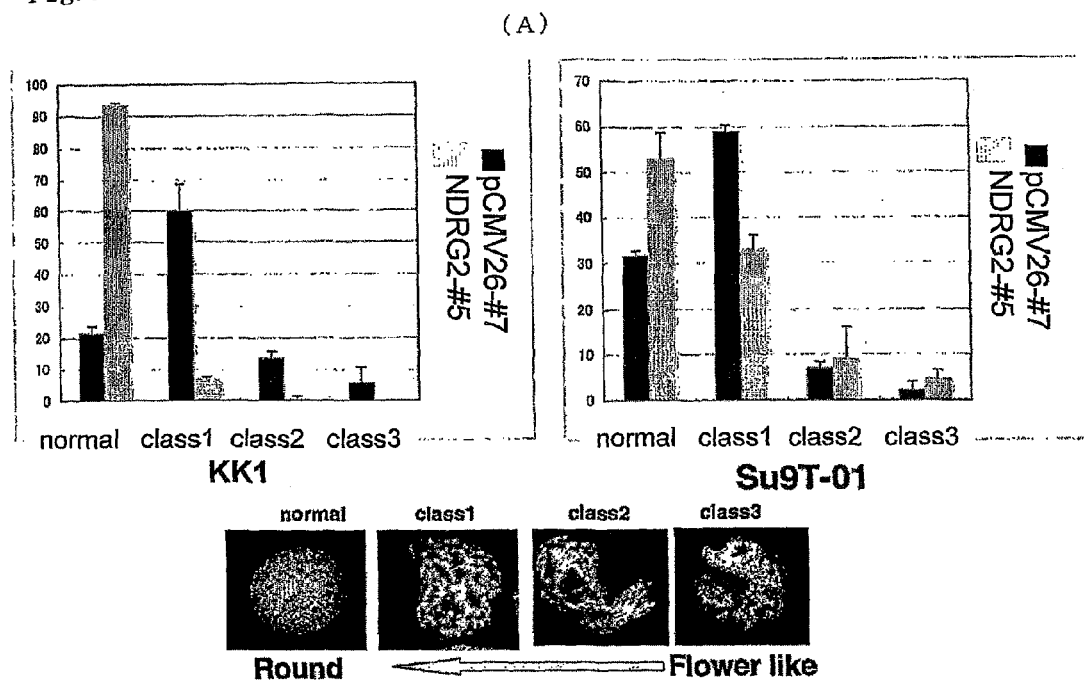
FIG. 17(A) shows graphs and photographs indicating the recover of nuclear deformation in ATL cell lines highly expressing NDRG2, and (B) shows a photograph indicating the release of nuclei in ATL cell lines highly expressing NDRG2 by the inhibition of tublin polymerization.
Figure 17:
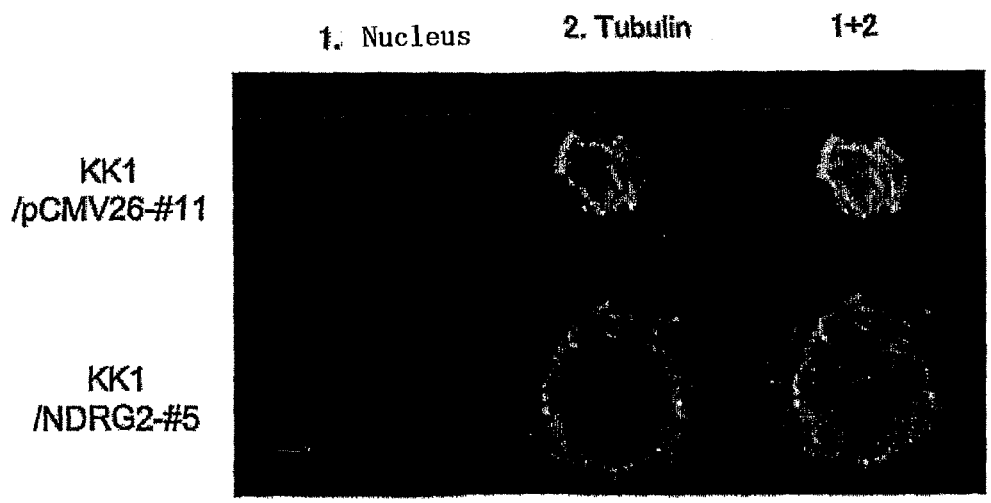
Figure 19:
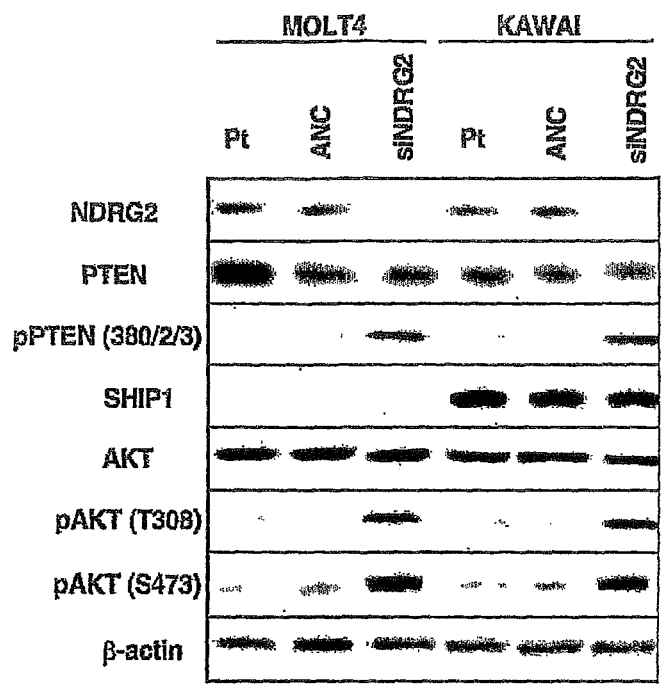
FIG. 19 shows the effect caused by the inhibition of NDRG2 gene expression, wherein (A) is a graph by the Western blot technique showing that the inhibition of NDRG2 gene expression against T-ALL cells promotes the activation of the P13K/AKT signaling pathway, and (B) shows graphs indicating the increased proliferation of the same cells.
Figure 19:
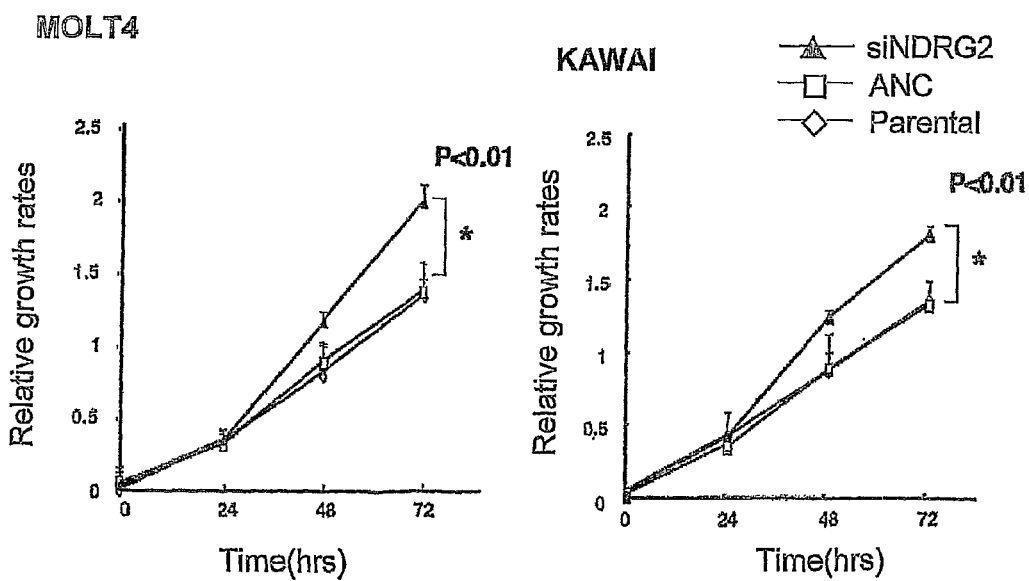

FIG. 19 indicates the dephosphorylation effect by NDRG2 from another aspect of FIGS. 15 to 17. In other words, as shown in FIG. 19(A), suppression of NDRG2 expression in the T-ALL cell lines promotes the phosphorylation of PTEN and AKT (pPTEN, pAKT). As is evident from the proliferation curve of cells in FIG. 19(B), cell proliferation is significantly increased by the suppression of NDRG2 expression compared to the control cells. Considering FIGS. 15 to 17 and FIG. 19 together, the original activity of PTEN is recovered and the activity by AKT phosphorylation is suppressed when NDRG2 gene is introduced into the ATL cell lines and highly expressed. These suggest that the dephosphorylating agent for PTEN comprising, as an active ingredient, NDRG2 according to the present invention may be useful as a gene therapeutic agent.

Pharmacological Effect of NDRG2 Protein; PTEN Dephosphorylation

Figure 11B:
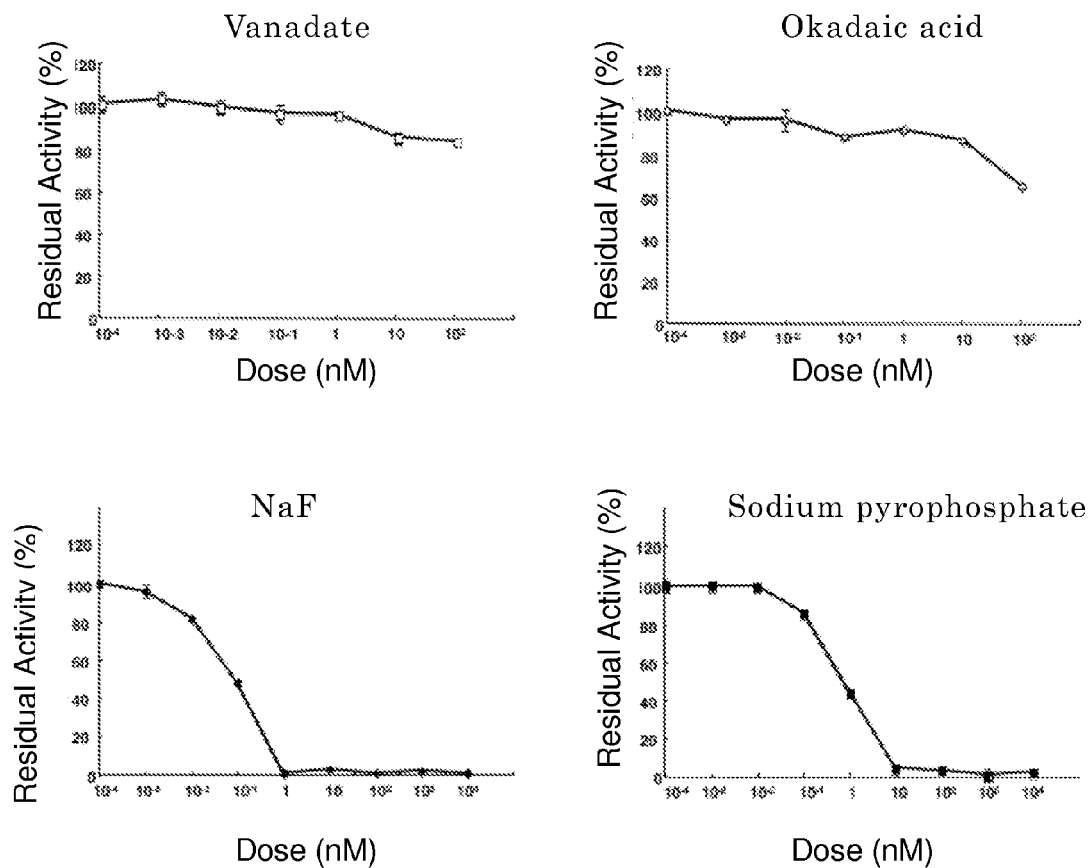

According to the present invention, as shown in FIG. 11, it is recognized that NDRG2 protein derived from $E.\ coli$ also shows the dephosphorylation effect on phosphorylated PTEN proteins derived from ATL cells, as with NDRG2 gene. That is, as shown in FIG. 11(A), NDRG2 has properties as a dephosphorylating enzyme like a phosphatase PP2A when estimated by the pNPP assay. In addition, when NDRG2 is investigated as an enzyme by the pNPP assay using four kinds of phosphatase inhibitors, only Ser/Thr phosphatase inhibitor has an enzyme inhibitory activity compared to protein phosphatase 2A (PP2A) as a control, as shown in FIG. 11(B). From this, NDRG2 is found to be an enzyme having an activity as a Ser/Thr phosphatase.

Furthermore, a synthetic peptide corresponding to 16-amino acid peptide including the S380/T382/T383 region of PTEN protein, wherein the three sites are respectively phosphorylated, is produced, and the phosphatase specificity on the peptide by NDRG2 protein is investigated. As shown in FIG. 12(A), the result exhibits that S382, S382/I383, and S380/1382/1383 undergo a selective dephosphorylation by NDRG2. On the other hand, PTEN protein is purified by the immunoprecipitation method with ATL cell lines, mixed with the GFP-NDRG2 fusion protein that has been produced in $E.\ coli$, and a phosphorylation status of PTEN protein using various PTEN phosphorylation antibodies after the reaction is examined. As shown in FIG. 12(B), the PTEN protein includes S370 and S385 in the ATL cells and S380/1382/1383 are also phosphorylated, but only S380, T382, and T383 are dephosphorylated by mixing with NDRG2, and S370 and S385 are not altered. FIG. 13(A) shows the dephosphorylation of phosphorylated peptides by NDRG2 according to the DOTBLOT method, and the result is derived from that various PTEN phosphorylated peptides are synthesized, and mixed with NDRG2 protein, and that dephosphorylation of the peptides is investigated using two kinds of antibodies against phosphorylated PTEN. This result elucidates that NDRG2 can dephosphorylate the phosphorylated peptides at the T382, T382/T383, and S380/T382/T383 residues, and cannot dephosphorylate the peptide wherein only S380 or only T383 is phosphorylated. Thus, NDRG2 is a phosphatase for PTEN, which recognizes only PTEN protein including the phosphorylation status of T382, and reacts with a substrate. Further, point mutation is inserted at the phosphorylation sites S380, T382, and T383 of PTEN protein in any combination thereof so that amino acid substitution is allowed to occur, and this PTEN mutated gene is introduced into HUT102 cells, and then the activation level of the P13K/AKT signaling pathway is investigated. As the result is shown in FIG. 13(B), if there exists any PTEN protein in a state where even one of these three phosphorylation sites is not phosphorylated, AKT is dephosphorylated. Thus, the original function of PTEN is recovered. In other words, at least from the viewpoint of phosphorylation of AKT, it is necessary for PTEN to be phosphorylated at all three sites, and conversely, the dephosphorylation of AKT can be achieved by dephosphorylating at least one site among the three sites of PTEN using NDRG2. FIG. 14 shows the study of the experiment performed in FIG. 13(B) from the standpoint of cell proliferation ability, and if at least one of the three phosphorylation sites of PTEN is phosphorylated, a significant decrease in the cell proliferation ability is seen, which supports the result of FIG. 13(B). Such dephosphorylation effect of NDRG2 is also effective for a cancer one of the causes of which is other P13K/AKT signaling pathway other than ATL.

Pharmacological Effect of NDRG2 Protein; Anticancer Effect

Figure 8:
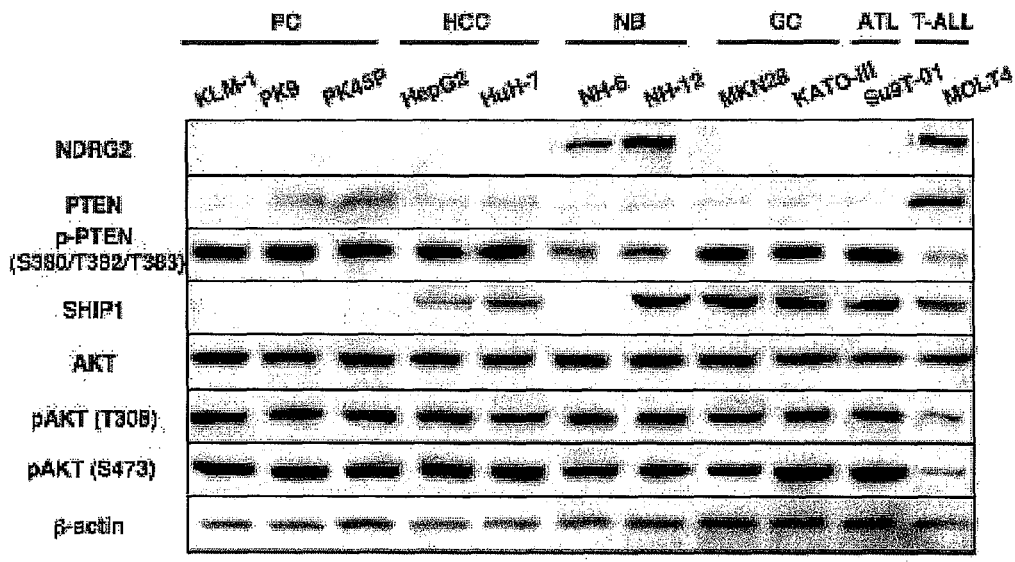
FIG. 8 shows the activation of the P13K/AKT signaling pathway due to decreased expression of NDRG2, wherein (A) is a photograph by the Western blot technique showing the expression of each protein in pancreatic cancer (PC), hepatocyte cancer (HCC), neuroblastoma (NB), and gastric cancer (GC), and (B) is a photograph by the Western blot technique showing the expression of each protein in liver cancer, cerebral tumor, breast cancer, colon cancer, uterine cancer, ovarian cancer, prostate cancer, and oral squamous cell cancer, other than as in (A).
Figure 8:
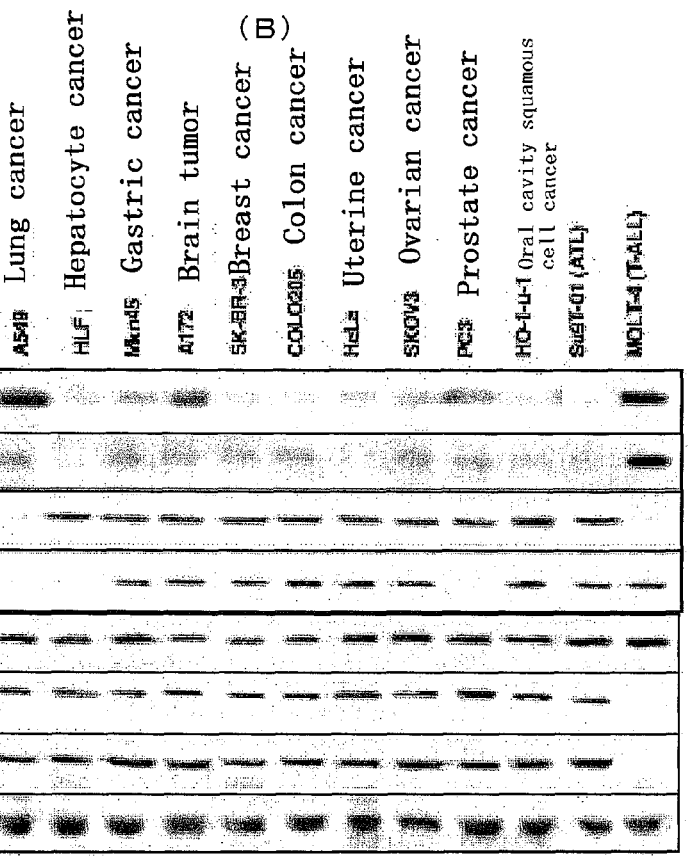

FIG. 8 shows the test result suggesting the possibility of anticancer effects of NDRG2 in many cancer cells, or as a preventive, progression inhibitor or therapeutic agent for a cancer. For example, as shown in FIG. 8(A), in many solid cancers including PC; pancreatic cancer, HCC; hepatocyte cancer, and GC; gastric cancer, decreased expressions of NDRG2 and PTEN proteins as well as abnormalities in the phosphorylation of PTEN protein are found, and AKT phosphorylation, i.e., the activation of the P13K/AKT signaling pathway can be seen. Similarly, in FIG. 8(B), there are decreased expressions of NDRG2 and PTEN proteins and abnormalities in the phosphorylation of PTEN protein, and AKT phosphorylation, i.e., the activation of the P13K/AKT signaling pathway is recognized in the cells of liver cancer, cerebral tumor, breast cancer, colon cancer, uterine cancer, ovarian cancer, prostate cancer, and oral squamous cell cancer other than as described in FIG. 8(A). FIG. 18(A) shows that high expression of NDRG2 also in pancreatic cancer cell lines indicates the dephosphorylation of PTEN.

These series of findings indicate that the dephosphorylating agent for PTEN comprising, as an active ingredient, NDRG2 of the present invention is effective against ATL, as well as various floating cancers and solid cancers the cause of which is the activation of the P13K/AKT signaling pathway. By the way, known cancers the cause of which is the activation of the P13K/AKT signaling pathway include ovarian cancer, lung cancer: Bellacosa A, Testa J R et al. Molecular alterations of the AKT2 oncogene in ovarian and breast carcinomas. Int. J. Cancer 64, 280-285 (1995), ovarian cancer: Shayesteh L, Gray J W et al. PIK3CA is implicated as an oncogene in ovarian cancer. Nature Genet. 21, 99-102 (1999); Philp A J, Phillips W A et al. The phosphatidylinositol 3'-kinase p85α gene is an oncogene in human ovarian and colon tumors. Cancer Res. 61, 7426-7429 (2001); Ringel M D, Saji M et al. Overexpression and overactivation of Akt in thyroid carcinoma. Cancer Res. 61, 6105-6111 (2001), pancreatic cancer: Cheng J Q, Testa J R et al. Amplification of AKT2 in human pancreatic cells and inhibition of AKT2 expression and tumorigenicity by antisense RNA. Proc. Natl Acad. Sci. USA 93, 3636-3641 (1996), pancreatic ductal adenocarcinoma: Ruggeri B A, Testa J R et al. Amplification and overexpression of the AKT2 oncogene in a subset of human pancreatic ductal adenocarcinomas. Mol. Carcinog. 21, 81-86 (1998)), gastric cancer: Byun D S, Chi S G et al. Frequent monoallelic deletion of PTEN and its reciprocal association with PIK3CA amplification in gastric carcinoma. Int. J. Cancer 104, 318-327 (2003), acute myeloid leukemia: Min Y H, Ko Y W et al. Constitutive phosphorylation of Akt/PKB protein in acute myeloid leukemia, its significance as a prognostic variable. Leukemia 17, 995-997 (2003), lung cancer, bronchial lesions: Balsara B R, Testa J R et al. Frequent activation of AKT in non-small cell lung carcinomas and preneoplastic bronchial lesions. Carcinogenesis 25, 2053-2059 (2004).

Interaction Between NDRG2 and PTEN

Figure 9:
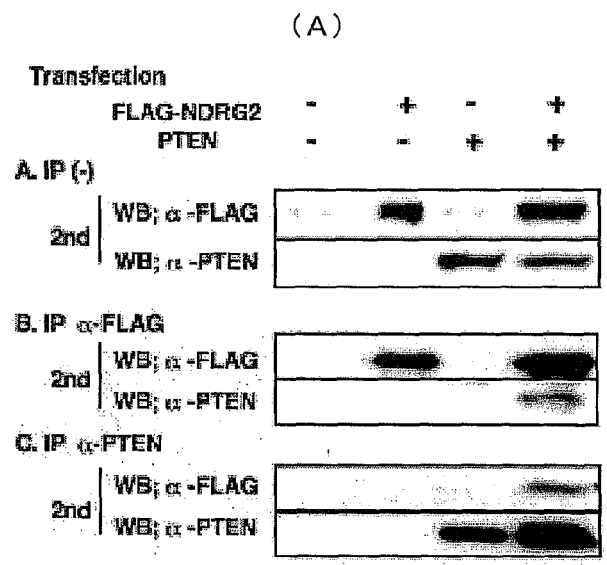
FIG. 9 shows states of PTEN and NDRG2 proteins in ATL cells, wherein (A) is a photograph by the immunoprecipitation/Western blot technique showing the binding of PTEN/NDRG2 when both of PTEN/NDRG2 are forcibly expressed in 293T cells, and (B) is a photograph by the immunoprecipitation/Western blot technique showing the binding of endogenous NDRG2 and PTEN in a normal state in a T-ALL cell line MOLT4.
Figure 9:
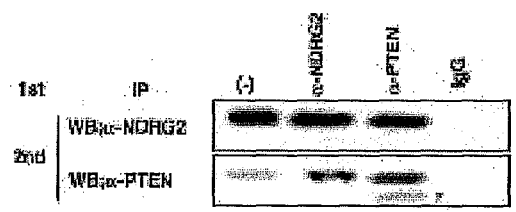

In order to confirm the phosphorylation-inhibiting effect of NDRG2/dephosphorylation effect thereof, the present inventors investigated the intermolecular interaction between NDRG2 and PTEN. At first, 293T cells were transfected with Flag-tagged NDRG2 and PTEN alone or simultaneously to confirm the presence or absence of overexpression. FIG. 9(A), panel A shows the result. As shown in the same Figure, NDRG2 and PTEN are overexpressed respectively in the immunoblotting with anti-FLAG antibody and anti-PTEN antibody. Next, 293T cells that had been transfected with Flag-tagged NDRG2 and PTEN alone or simultaneously and then overexpressed were subjected to immunoprecipitation with anti-FLAG antibody or anti-PTEN antibody, and NDRG2 and PTEN were detected with respective antibody. FIG. 9(A), panel B shows the result. As shown in the same Figure, bands can be confirmed by immunoprecipitation detection with anti-Flag antibody. As a result of immunoprecipitation with anti-PTEN antibody, the bands can be similarly confirmed as shown in FIG. 9(A), panel C. From these, it is possible to infer that there is an interaction between NDRG2 and PTEN in the high expression system of NDRG2, and the phosphorylation inhibition/dephosphorylation for PTEN are performed through the high expression of NDRG2.

Binding of NDRG2 to PTEN

FIG. 9(B) shows the binding of endogenous NDRG2/PTEN proteins in MOLT4 (T-ALL) cell line. That is, as is apparent from FIG. 9(B), even if one of NDRG2 and PTEN is allowed to be precipitated according to the coimmunoprecipitation method, the other is precipitated accompanying the former, and this indicates that both are endogenously bound. Moreover, FIG. 10 shows the identical localization of intracellular NDRG2 and PTEN as estimated by an immunofluorescence staining. In the Figure, as the result of observation of green color-labeled NDRG2 and red color-labeled PTEN, a yellow overlapping part is observed. This indicates the identical localization of NDRG2 and PTEN. Interestingly, distribution of the localization of NDRG2 and PTEN varies by the high expression of NDRG2, and the nuclear shape becomes close to the normal round shape from the petal type. PTEN nuclear import by mono-ubiquitination with NEDD4-1 has been reported (Trotman L C et al. Ubiquitination regulates PTEN nuclear import and tumor suppression. Cell. 2007; 128: 141-156), and present observation reveals the possibility that NDRG2 is also involved in PTEN nuclear import.

The invention claimed is:

1. A method of treating Adult T-cell leukemia (ATL), comprising administering to a subject in need of such treatment a cDNA encoding N-Myc downstream-regulated gene 2 protein (NDRG2).

2. The method of treating ATL according to claim 1, wherein the cDNA is introduced in ATL cells.

3. A method of treating ATL, comprising administering to a subject in need of such treatment a NDRG2.

4. The method of treating ATL according to claim 3, wherein said NDRG2 protein is expressed in ATL cells.

* * * * *

UNITED STATES PATENT AND TRADEMARK OFFICE
CERTIFICATE OF CORRECTION

PATENT NO. : 9,023,343 B2
APPLICATION NO. : 13/263876
DATED : May 5, 2015
INVENTOR(S) : Kazuhiro Morishita et al.

It is certified that error appears in the above-identified patent and that said Letters Patent is hereby corrected as shown below:

Title Page

In column 2 (page 1, item 56) at line 29, Under Other Publications, change "supressor" to --suppressor--.

Page 1 (item 57, Abstract) at line 4, Change "P13K" to --PI3K--.

In the Specification

In column 1 at line 23 (approx.), Change "P13K" to --PI3K--.
In column 1 at line 25, Change "P13K" to --PI3K--.
In column 1 at line 36, Change "P13" to --PI3--.
In column 1 at line 36, Change "(P13K)" to --(PI3K)--.
In column 1 at line 41, Change "P13K" to --PI3K--.
In column 1 at line 44, Change "P13K" to --PI3K--.
In column 1 at line 46, Change "P13K" to --PI3K--.
In column 2 at line 29, Change "P13K" to --PI3K--.
In column 2 at line 39, Change "P13K" to --PI3K--.
In column 2 at line 59, Change "P13K" to --PI3K--.
In column 3 at line 21, Change "P13K" to --PI3K--.
In column 3 at line 27, Change "P13K" to --PI3K--.
In column 3 at line 52, Change "P13K" to --PI3K--.
In column 3 at line 57, Change "P13K" to --PI3K--.
In column 4 at line 2, Change "P13K" to --PI3K--.
In column 4 at line 3, Change "P13K" to --PI3K--.
In column 4 at line 16 (approx.), Change "P13K" to --PI3K--.
In column 4 at line 18 (approx.), Change "P13K" to --PI3K--.

Signed and Sealed this
Eighth Day of March, 2016

Michelle K. Lee
*Director of the United States Patent and Trademark Office*

CERTIFICATE OF CORRECTION (continued)
U.S. Pat. No. 9,023,343 B2

In the Specification

In column 4 at line 19, Change "P13K" to --PI3K--.

In column 4 at line 21, Change "P13K" to --PI3K--.

In column 4 at line 54, Change "P13K" to --PI3K--.

In column 4 at line 60, Change "P13K" to --PI3K--.

In column 4 at line 66, Change "recover" to --recovery--.

In column 5 at line 2, Change "recover" to --recovery--.

In column 5 at line 5, Change "tublin" to --tubulin--.

In column 5 at line 6, Change "P13K" to --PI3K--.

In column 5 at line 17, Change "P13K" to --PI3K--.

In column 6 at line 63, Change "P13K" to --PI3K--.

In column 6 at line 66, Change "P13K" to --PI3K--.

In column 7 at line 38, Change "P13K" to --PI3K--.

In column 7 at line 54, Change "P13K" to --PI3K--.

In column 8 at lines 22-23, Change "Parvoviridiae, Picornoviridiae, Herpesveridiae, Poxyiridae, Adenoviridiae," to --Parvoviridae, Picornaviridae, Herpesviridae, Poxviridae, Adenoviridae,--.

In column 8 at line 23, Change "Picornnaviridiae" to --Picornaviridae--.

In column 11 at line 44, Change "P13K" to --PI3K--.

In column 11 at line 47, Change "P13K" to --PI3K--.

In column 11 at line 48, Change "P13K" to --PI3K--.

In column 11 at line 51, Change "P13K" to --PI3K--.

In column 11 at line 52, Change "P13K" to --PI3K--.

In column 11 at line 59, Change "P13K" to --PI3K--.

In column 12 at line 4, Change "P13K" to --PI3K--.

In column 12 at line 8, Change "P13K" to --PI3K--.

In column 12 at line 15, Change "P13K" to --PI3K--.

In column 12 at line 18, Change "P13K" to --PI3K--.

In column 12 at line 20, Change "P13K" to --PI3K--.

In column 13 at line 8, Change "(Maack" to --(Mack--.

In column 14 at line 3, Change "GREEN®" to --GREEN (R)--.

In column 14 at line 7 (approx.), Change "PRISM®" to --PRISM (R)--.

In column 14 at line 24, Change "SiT," to --S1T,--.

In column 15 at line 26 (approx.), Change "TaniwakiM," to --Taniwaki M,--.

In column 15 at line 37 (approx.), Change "Vectaschield;" to --Vectashield;--.

CERTIFICATE OF CORRECTION (continued)
U.S. Pat. No. 9,023,343 B2

In the Specification

In column 15 at line 51 (approx.), Change "(Affymertix)." to --(Affymetrix).--.

In column 16 at line 39, Change "(DakoCytomation)," to --(Dako Cytomation),--.

In column 16 at line 63, Change "Signal®" to --Signal (R)--.

In column 19 at line 10, Change "NaGH," to --NaOH,--.

In column 20 at line 27, Change "Signal®" to --Signal (R)--.

In column 20 at line 31, Change "Signal®" to --Signal (R)--.

In column 20 at line 48, Change "P13K" to --PI3K--.

In column 21 at line 11, Change "P13K" to --PI3K--.

In column 22 at line 65, Change "P13K" to --PI3K--.

In column 23 at line 24, Change "tublin" to --tubulin--.

In column 25 at line 45, Change "P13K" to --PI3K--.

In column 25 at line 50, Change "P13K" to --PI3K--.

In column 25 at line 52, Change "P13K" to --PI3K--.

In column 26 at line 39, Change "1383," to --T383,--.

In column 26 at line 40, Change "1382/1383" to --T382/T383--.

In column 26 at line 47, Change "1382/1383" to --T382/T383--.

In column 26 at line 67, Change "P13K" to --PI3K--.

In column 27 at line 17, Change "P13K" to --PI3K--.

In column 27 at line 28, Change "P13K" to --PI3K--.

In column 27 at line 32, Change "P13K" to --PI3K--.

In column 27 at line 43, Change "P13K" to --PI3K--.

In column 27 at line 45, Change "P13K" to --PI3K--.